(12) United States Patent
Makeig et al.

(10) Patent No.: US 7,254,500 B2
(45) Date of Patent: Aug. 7, 2007

(54) MONITORING AND REPRESENTING COMPLEX SIGNALS

(75) Inventors: Scott Makeig, Cardiff, CA (US); Jörn Anemüller, La Jolla, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 72 days.

(21) Appl. No.: 10/816,568

(22) Filed: Mar. 31, 2004

(65) Prior Publication Data

US 2005/0007091 A1    Jan. 13, 2005

Related U.S. Application Data

(60) Provisional application No. 60/459,930, filed on Mar. 31, 2003.

(51) Int. Cl.
*G01R 23/00* (2006.01)

(52) U.S. Cl. .............................. 702/75; 702/65; 702/66; 702/67; 702/68; 702/69; 702/70; 702/73; 702/74; 702/75; 702/76; 702/77; 702/189; 702/190; 702/191; 702/194; 324/76.19

(58) Field of Classification Search ............ 702/66–77, 702/189–191, 194; 324/536, 76.19
See application file for complete search history.

(56) References Cited

U.S. PATENT DOCUMENTS 5,383,164 A    1/1995   Sejnowski et al.
6,424,960 B1 *  7/2002   Lee et al. ...................... 706/20
6,957,172 B2 * 10/2005   Wegerich ..................... 702/189
2003/0061035 A1 *  3/2003   Kadambe .................... 704/203

OTHER PUBLICATIONS

J. Anemüller, "Across-Frequency Processing in Convolutive Blind Source Seperation", PhD thesis, Department of Physics, University of Oldenburg, Oldenburg Germany, Jul. 30, 2001, 107 pgs.
T. Jung et al., "Imaging Brain Dynamics Using Independent Component Analysis", Proceedings of the IEEE, vol. 89, No. 7, Jul. 2001, pp. 1107-1122.
J. Martin, "The Collective Electrical Behavior of Cortical Neurons: The Electroencephalogram and the Mechanisms of Epilepsy", Principles of neural science, 3rd Ed. Elsevier, 1991, pp. 777-791.
K. Torkkola, "Blind Signal Separation In Communications: Making Use Of Known Signal Distributions", IEEE DSP Workshop, Bryce Canyon, UT, Aug. 10-12, 1998, pp. 1-4.

* cited by examiner

*Primary Examiner*—Marc S. Hoff
*Assistant Examiner*—Phuong Huynh
(74) *Attorney, Agent, or Firm*—Morrison & Foerster LLP

(57) ABSTRACT

A method of displaying signals containing a spatial and a temporal aspect, where multiple signals are received by multiple sensors. The received signals are decomposed into separate signal components within one or more distinct frequency bands. Signal components are isolated within each frequency band based on differences between the signal components within the same frequency band, and the signal components are displayed. The signal components may be analyzed to determine a time course of activity and a location of the associated source. Representations of the source may also be generated and displayed to aid in monitoring the signals.

32 Claims, 20 Drawing Sheets

MONITORING AND REPRESENTING COMPLEX SIGNALS

CROSS-REFERENCE TO RELATED APPLICATIONS

This application claims the benefit of provisional application 60/459,930, filed Mar. 31, 2003, and incorporated herein in its entirety by reference.

GOVERNMENTAL INTEREST

This invention was made with support under grant number 1R01MH/RR61619-01 from the National Institutes of Health. The Government may have rights in this invention.

BACKGROUND OF THE INVENTION

1. Field of the Invention

This invention relates to monitoring and analyzing complex signals, and in particular, to separating and displaying the independent signal components of complex signals from a signal source.

2. Description of the Related Art

There are many reasons why it is useful to separate specific signals from a mixture of signals. For example, one may wish to separate a single speaker from a mixture of sound signals. In another instance, a physician may wish to isolate and study a single signal from an organ from other signals generated by the same organ. However, separating independent signals that are part of a mixture of signals is a well-studied, but challenging area of signal processing. Typically, the signal sources and their mixing characteristics are unknown. Without knowledge of the signal sources, other than the general assumption that they come from independent sources, the signal processing problem is referred to as "blind separation of sources." The separation is "blind" because nothing is known about the frequency or phase of the signals from the independent source.

One area that has benefited from signal separation technologies is the area of medical signal processing. For example, since its discovery in the 1920's, the study of electroencephalographic (EEG) data recorded from the human scalp has been frustrated by the fact that each scalp electrode receives the sum of electrical activities taking place in many different parts of the brain, and that separation of these signals is difficult to perform. U.S. Pat. No. 5,383,164, issued to Sejnowski and Bell in 1995, discloses a blind source separation method using the technique of independent component analysis (ICA) and incorporating an information maximizing ("infomax") principle. This method of separating mixed signals from a plurality of sensors is now commonly referred to as "infomax ICA." Infomax ICA has been used to process EEG data received with multiple sensors, for example, attached to the scalp, thus allowing separation of electrical signals originating in different unknown signal sources in the brain. By identifying individual signal sources, physicians were then able to identify the physical signal source of the EEG signals, or "effective source" in the brain.

Although infomax ICA has been used to analyze EEG signals, it relies on several idealized assumptions about the underlying signal sources that may not be completely realistic. For example, in infomax ICA, the EEG signal sources are analyzed as if they come from spatially fixed brain locations and have perfectly synchronized activity across the whole domain of brain cortical activity associated with each signal source. In some operational settings, these idealized assumptions may limit the ability to adequately capture underlying complex spatio-temporal dynamics.

Therefore, there is a need for improved methods and systems for analyzing complex signals and for separating component signals from a mixture of signals.

SUMMARY OF THE INVENTION

This invention comprises methods and devices for monitoring and displaying complex signals. According to one embodiment, the invention comprises a method of monitoring signals, comprising receiving signals from a plurality of sensors over a specified period of time, decomposing the signals into separate signal components within one or more frequency bands, selecting a frequency band within the one or more frequency bands, determining spatial and temporal characteristics of the signal components within the first frequency band, isolating a subset of the signal components within the frequency band, based on spatial and temporal characteristics of the signal components to determine a subset of signal components emanating from a signal source, and displaying the isolated signal components, thereby monitoring the signals.

According to another embodiment, the invention comprises a method of displaying biological signals generated from a first biological signal source, comprising receiving a plurality of signals from a plurality of biological signal sources, decomposing the received plurality of signals into biological signal components within one or more frequency bands, selecting a first frequency band in the one or more frequency bands, determining spatial and temporal characteristics of the biological signal components within the first frequency band, isolating a subset of the biological signal components within the first frequency band, based on spatial and temporal characteristics of the biological signal components, to obtain isolated biological signal components generated by the first signal source, and displaying the isolated biological signal components generated by the first signal source.

According to another embodiment, the invention comprises a system for displaying biological signals on a computer display, comprising a plurality of sensors for receiving biological signals, a first memory configured to decompose the received plurality of signals into separate signal components within one or more frequency bands and select a first frequency band, a second memory configured to determine spatial and temporal characteristics of the biological signal components in the first frequency band, a third memory configured to isolate a subset of the biological signal components within the first frequency bands, based on spatial and temporal characteristics of the biological signal components, to obtain isolated biological signal components, and a display for displaying the isolated biological signal components.

According to yet another embodiment, the invention comprises a computer-readable medium containing instructions for controlling a computer system that when run perform a method, comprising receiving biological signals from a plurality of sensors over a specified period of time, decomposing the biological signals into separate biological signal components within one or more frequency bands, selecting a first frequency band within the one or more frequency bands, determining spatial and temporal characteristics of the biological signal components within the first frequency band, isolating a subset of the biological signal components within the first frequency band, based on spatial and temporal characteristics of the biological signal components, to obtain isolated biological signal components, and displaying the isolated biological signal components.

According to yet another embodiment, the invention comprises a method of identifying signals generated by a signal source, wherein the signals are in different frequency bands, comprising receiving a plurality of signals from a plurality of sensors, decomposing the received plurality of signals into signal components within a plurality of frequency bands, identifying a first set of signal components in a first frequency band that are generated by the signal source, and a second set of signal components in a second frequency band that are also generated by the signal source, producing a first signal group comprising the first set of signal components and the second set of signal components, and identifying the signal activity of the signal source by measuring the signals in the signal group.

In this way, the present invention enables improved methods and systems for analyzing complex signals and for separating component signals from a mixture of signals.

BRIEF DESCRIPTION OF THE DRAWINGS

The above-mentioned and other features and advantages of the invention will become more fully apparent from the following detailed description, the appended claims, and in connection with the accompanying drawings in which:

DETAILED DESCRIPTION OF EXEMPLARY EMBODIMENTS

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

According to one embodiment, the invention comprises specialized processing methods, termed herein "complex ICA" or "complex independent component analysis" for determining independent signals from a mixture of signals, thus isolating a signal or a signal component from the mixture of signals. Typically, the mixture of signals is received from a plurality of sensors. In one example, the sensors are EEG or Electrocardiogram (ECG) sensors. Unlike prior signal separation techniques, the complex ICA processing methods described herein do not assume that the signal source is a fixed location, but rather make no assumption about the intrinsic spatio-temporal dynamics of the signal. By not making any assumptions about the location of the signal source during a specified period of time, the signals can be separated and monitored more accurately. The mechanism by which complex ICA analyzes data in order to preserve the spatio-temporal component is explained more fully below.

Figure 1:
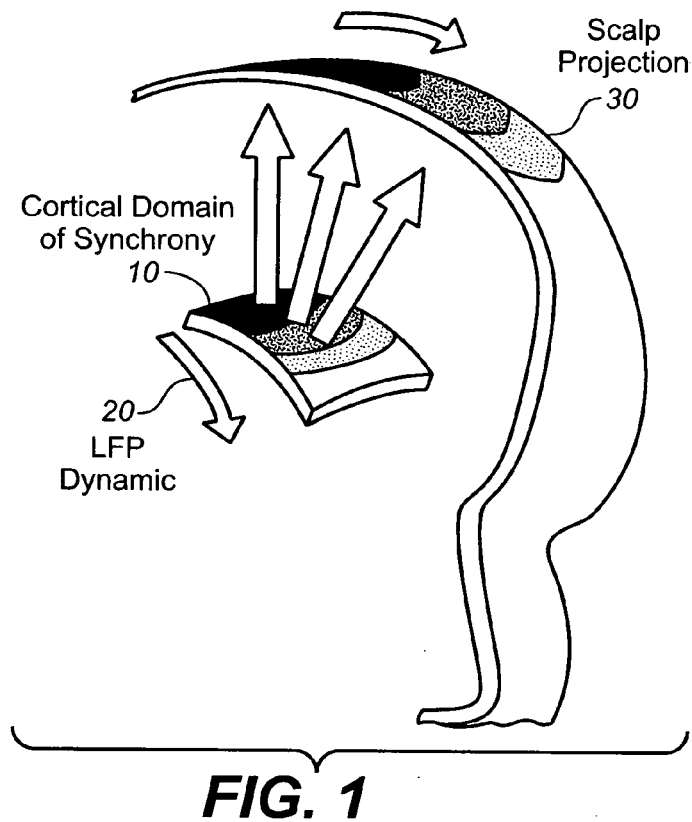
FIG. 1 is an illustration of a spatio-temporal flow on a brain cortex, according to one embodiment of the invention.

As used herein, "spatio-temporal signals" or "spatial-temporal dynamics" include those signals or processes that have both spatial and temporal characteristics. As used herein, a spatial characteristic of a signal is a feature of that signal that represents physical movement associated with the signal in space. Thus, the features of a signal that represent its movement in space are spatial characteristics of a signal. As used herein, a temporal characteristic describes a time dependency feature associated with the signal. For example, a signal generated over a period of time; and by a moving source, would be a spatio-temporal signal that would have spatial characteristics and temporal characteristics. FIG. 1 shows, for example, a representation of a spatio-temporal signal flow from a source on the brain cortex. The cortical domain of synchrony 10 illustrates the source location where the spatio-temporal flow of electric signals across an area of brain cortex occurs. A local field potential (LFP) 20 may correspondingly vary with the signal flow across the cortical domain 10 generating detectable spatio-temporal signals. The scalp projection 30 illustrates the spatio-temporal signal projection of the signals onto the scalp, which is detectable by appropriately positioned sensors, e.g., scalp electrodes.

As discussed above, in one embodiment of the invention the signals received with the plurality of sensors comprise electroencephalographic (EEG) signals. Typically, a plurality of sensors includes between 3 and 256 sensors to record EEG signal data. However, the plurality of sensors may also include 8, 16 or 32 sensors. The invention, however, is not limited to applications where the received signals comprise EEG data. For example, embodiments of the invention may include the use of complex ICA to analyze and monitor other types of mixed signals received by multiple sensors from multiple sources. Examples of other mixed signals include other biological signals, such as magnetoencephalographic, electrocardiographic, electromyographic, and electrogastric signal data, magnetic resonance imaging, positron emission tomography and optical imaging. In addition, embodiments of the invention include separation of non-biological signal data that also exhibit spatio-temporal dynamics, such as communication signals.

Embodiments of this invention may include complex ICA techniques that calculate the intrinsic spatio-temporal dynamics of the effective signal sources, as described here. In one embodiment, the spatio-temporal dynamics include flow patterns of signals, and the complex ICA utilizes a "convolutive," rather than an "instantaneous," signal mixing model for processing the received signals. When using the convolutive model, the strength of a signal is calculated by analyzing the measured signal received by the plurality of sensors, and then taking into account a portion of the signal that is received by the plurality of sensors at a different time, or in a different portion of the data. This is useful for measuring source signals that are generated along a flow pattern, or pathway, and not at a fixed point.

In some cases, the flow pattern of each signal source is essentially always the same. This type of signal activity is called "stereotyped current flow." As one example, within the brain, formulation of the signal source may result in signal waves that travel quickly across millimeters of brain cortex. Stereotyped current flows within the brain cortex generate corresponding EEG signals that can be detected by a plurality of scalp sensors. Implementation of the complex ICA systems and methods described herein allows these signals to be accurately measured with non-invasive methods, such as multiple electrodes or sensors placed on the scalp. Accordingly, embodiments of the invention provide a means for effectively recording, analyzing and displaying cortex activity that occurs in waves across a spatial region of the brain. This allows an investigator to determine a single EEG component and elicit a repeating or "looping sequence" of potential cortical activity maps with varying spatial topography. Through the methods and systems described herein, signals that were previously inseparable, or inaccurately separated, using instantaneous ICA can now be separated. This allows a greater spatial resolution of the participating signal sources in the brain to be obtained so that one can more finely determine the locations of cells participating in generating the signal activity.

As is known, EEG activity may occur with distinctive characteristics in different frequency bands, such as delta, theta, alpha, beta, sigma and gamma which may be associated with different physiological processes. For example, the delta frequency band of about 0–4 Hz is the slowest of all the brain wave frequencies and is most commonly associated with deep sleep. The theta frequency band of about 4–7 Hz is normally only experienced fleetingly as a person is waking, or drifting off to sleep. The alpha frequency band range of about 8–13 Hz is generally present when the brain is alert but unfocused, and is often associated with feelings of relaxation and calmness. The beta frequency band range of about 13–30 Hz is generally associated with peak concentration, heightened alertness, hand eye coordination and visual acuity. The gamma frequency range of about 30–90 Hz is generally associated with higher mental activity, including perception and consciousness, and is also generally associated with binding sensory inputs into the single, unitary object we perceive. The sigma band is not as commonly used but may be defined as 12–16 Hz, and is generally associated with a low level of concentration. Other less commonly defined frequency bands may also contain signal components with distinctive characteristics of the signals. Within the different frequency bands, there may be different domains of synchrony and/or flow patterns underlying the EEG data.

One embodiment of the invention is a method of monitoring signals by receiving a plurality of signals from a plurality of sensors. The received signals are then decomposed into signal components within separate frequency bands. This is referred to as "spectral decomposition" or "frequency decomposition." Once the signals are decomposed into separate frequency bands, one frequency band is selected and the spatial and temporal characteristics of the signal components within that frequency band are determined by the methods described below. A subset of signal components within the selected frequency band is then isolated by performing complex ICA on the signal components within the selected frequency, and maximizing the differences between the subset of signal components, and the other signals within the selected frequency band. The subset of signal components can then be displayed in order to monitor the signals generated by the signal source.

Another embodiment of the invention is a method for monitoring and displaying the location and time course of activity of a signal. In this method, signals are received, by a system, at multiple locations from a localized area and then decomposed into signal components within one or more distinct frequency bands. The signal components are analyzed within a frequency band to determine the location and time course of activity of a corresponding source. Representations depicting the signals received at the multiple locations from the corresponding source are generated to monitor the location and time course of activity of the source.

Another embodiment of the invention is a computer-readable medium containing instructions for controlling a computer system to monitor recorded signal data. The monitoring is done by receiving signals with a plurality of sensors, and decomposing these signals into separate signal components within one or more distinct frequency bands. The system also isolates a signal component, that has a spatial aspect and a temporal aspect different from other signal components within the same frequency, from the other signal components in the frequency band. The system then monitors the isolated signal component.

Another embodiment of the invention is a program storage device readable by a machine, tangibly embodying a program of instructions executable by the machine to perform a method for monitoring a source. This method includes receiving signals with a plurality of sensors, decomposing the received plurality of signals into separate signal components within one or more distinct frequency bands, isolating a first signal component, where the spatial aspect and a temporal aspect of the first signal component is different from other signal components within the same frequency band, and monitoring the first signal component.

In a different embodiment, signal sources that generate signals in multiple frequency bands can be identified and monitored by grouping signal components that occur in separate frequency bands. These grouped signal components are then analyzed to identify the location and a time course of activity of a signal source that produced the grouped signal components. "A time course of activity" as used herein refers to the complex independent activation timecourses produced by performing complex ICA, as described in further detail with the description of complex ICA below. The time course of activity describes the strength, or magnitude, of a signal source and the phase of the source as a function of time. The complex ICA process produces separate sets of independent components within distinct frequency bands. For example, some signal sources might produce signals in only one frequency band. However, other signal sources may generate signals in a broader frequency range, comprising signals generated in contiguous or disconnected frequency bands.

Since ICA analysis of a single frequency band would not take into account signals that may produce cross-over signals in more than one frequency band, this embodiment would capture signals that are generated across frequency bands. To obtain a complete picture of the underlying source processes, it is desirable to identify and group together those signal components that are transmitted from the same signal source, but in different frequency bands.

Accordingly, in one aspect of this embodiment, a plurality of signals are received from a plurality of sensors and the signals are decomposed into signal components in a plurality of frequency bands. A subset of signal components in a frequency band that were generated from a same source are identified, and another subset of signal components in a different frequency band that were also generated by the same source are identified. The subset of signal components may be a single signal component, or multiple signal components. The subsets of signal components from the different frequency bands are clustered together to form a group, and the signal activity of the signal source is identified by measuring the signals in the signal group. A group of similar signals is then clustered together into a group. Then, the group of biological signal components is analyzed to monitor the signal source of the grouped biological signal components.

Embodiments of the invention are described hereinbelow primarily with reference to EEG signals received with a plurality of sensors, or electrodes. It will be appreciated, however, that the invention can be practiced in many ways on a variety of signal data, and therefore the scope of the invention should be construed in accordance with the appended claims and any equivalents thereof.

Signal Source

As used herein, a signal source is any source of a signal that can be monitored. Examples of signal sources include body organs, such as the brain and heart. Other examples of signal sources include devices that emanate sounds, such as microphones, and devices that produce coherent light, such as fiber optic communication networks.

Biological Signals

Biological signals are signals that come from a living organism. Examples include signals generated by specific organs, such as the brain or heart, muscles. Other examples include information signals derived from biological matter such as information signals corresponding to the concentrations of oxyhemoglobin in parts of the brain. In this example, the signal source would correspond to the tissue volume where the oxyhemoglobin concentrations occur.

Biological Signal Component

A biological signal component, is a subset of biological signals. The subset might only include a single biological signal. For example, for EEG signals, a biological signal component may be the subset of biological signals in a specific frequency band, such as delta, alpha, beta, theta, sigma or gamma bands. Typically, a biological signal component is a subset of the mixture of biological signals that are generated by a single signal source.

Complex ICA

The definition of "complex ICA" is a variant of an infomax independent component analysis (ICA) process that uses complex numbers to determine separate signals within a group of signals (e.g., through a frequency-domain characterization). The use of complex numbers to maximize the differences between input signals allows the representation of signal flows ("phases") over time to be associated with a single signal source.

Component Activation

Component Activation is a representation of the activity of a source, for example, in terms of its strength and phase. For example, with EEG data, when a source becomes "active" it produces signals that are received with multiple sensors. The signals may be separated into signal components in different frequency bands. Performing complex ICA on each frequency band yields a component activation for each signal component, that is, the strength and the phase of a source that produced that signal component. The component activation may be described as a "map" by representing the strength and phase of a source of a signal component at each sensor.

Component Map

A component map is a graphical representation of the measured values received at multiple sensor locations that are attributable to a signal component.

Input Devices

An input device can be, for example, a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touch-screen.

Instructions

Instructions refer to computer-implemented steps for processing information in the system. Instructions can be implemented in software, firmware or hardware and include any type of programmed step undertaken by components of the system.

LAN

One example of the Local Area Network may be a corporate computing network, including access to the Internet, to which computers and computing devices comprising the system are connected. In one embodiment, the LAN conforms to the Transmission Control Protocol/Internet Protocol (TCP/IP) industry standard. In alternative embodiments, the LAN may conform to other network standards, including, but not limited to, the International Standards Organization's Open Systems Interconnection, IBM's SNA, Novell's Netware, and Banyan VINES.

Media

Media refers to images, sounds, video or any other multimedia type data that is entered into the preferred system. Typically media refers to a document that is entered into the system by a document scanner.

Microprocessor

The microprocessor may be any conventional general purpose single- or multi-chip microprocessor such as a Pentium® processor, a Pentium® Pro processor, a 8051 processor, a MIPS® processor, a Power PC® processor, or an ALPHA® processor. In addition, the microprocessor may be any conventional special purpose microprocessor such as a digital signal processor or a graphics processor. The microprocessor typically has conventional address lines, conventional data lines, and one or more conventional control lines.

Modules

The system comprises various modules as discussed in detail below. As can be appreciated by one of ordinary skill in the art, each of the modules comprises various subroutines, procedures, definitional statements and macros. Each of the modules is typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

Networks

The system may include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value added network, an intranet, and the like.

Operating Systems

The system may be used in connection with various operating systems such as: UNIX, Disk Operating System (DOS), OS/2, Windows 3.X, Windows 95, Windows 98, and Windows NT.

Programming Languages

The system may be written in any programming language such as C, C++, BASIC, Pascal, Java, and FORTRAN and run under any of the well-known operating systems. C, C++, BASIC, Pascal, Java, and FORTRAN are industry standard programming languages for which many commercial compilers can be used to create executable code.

System Overview

Figure 2:
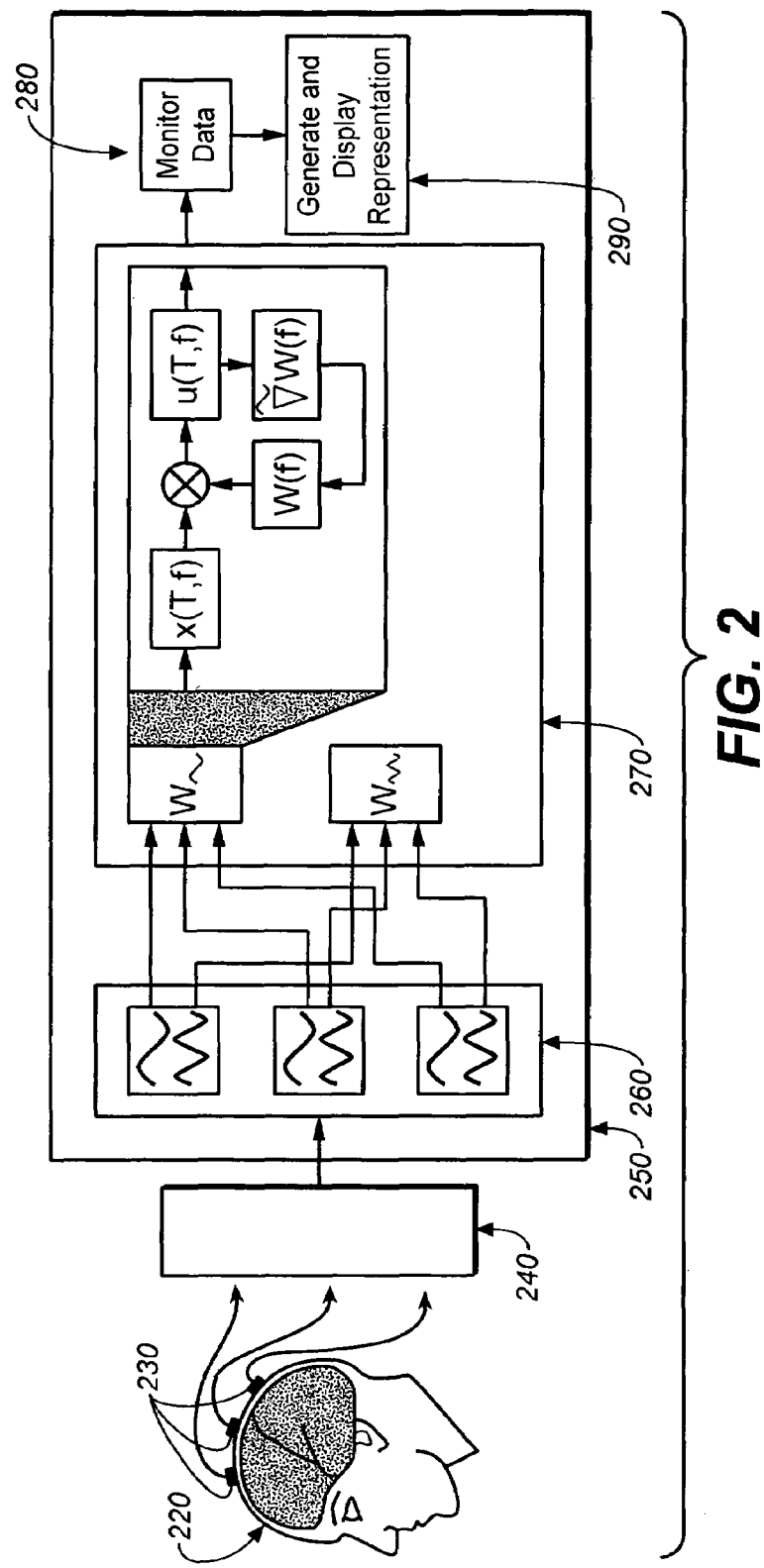
FIG. 2 is a diagram illustrating the signal monitoring process, according to one embodiment of the invention.

FIG. 2 illustrates a simplified representation of receiving EEG signals with multiple sensors 230 connected to a scalp 220 in which the complex ICA method may be employed, according to one embodiment of the invention. The sensors 230 receive a plurality of EEG signals and provide the received signals to a signal recorder 240. A signal recorder 240 may be used to record the signals and then provide the recorded signal data to a computer 250. Methods and systems for receiving EEG signals using a plurality of sensors and recording the received signals are well known in the art and therefore are not described herein.

The signal recorder 240 provides the received signal data to a computer 250 that processes the signals. EEG signals are typically recorded and then subsequently processed and analyzed. However, the received signals also may be communicated to a computer 250 for processing in real-time or near real-time, without the use of a signal recorder 240, according to another embodiment. Alternatively, the received signals may be communicated to a computer 250, stored in memory (e.g., as illustrated by the memory 320 shown in FIG. 3), and then subsequently processed, according to another embodiment.

The computer 250 may be any data processor controlled device, including a video terminal device, such as a personal computer, a workstation, a server, a minicomputer, a mainframe computer or a laptop computer. In addition, the computer 250 can be connected to a network of individual computers, mobile computers, palm-top computers, handheld computers, or other type of computing devices capable of performing signal processing. The computer 250 may be a uni-processor or a multi-processor machine. Additionally, the computer may include an addressable storage medium or computer accessible medium, such as random access memory (RAM), an electronically erasable programmable read-only memory (EEPROM), programmable read-only memory (PROM), erasable programmable read-only memory (EPROM), hard disk, floppy disk, laser disk player, digital video device, compact disks, video tape, audio tape, or magnetic recording track. In addition, the computer 250 can be connected through an electronic network in order to transmit, receive or store electronic content such as, by way of example, programs and data.

In one embodiment, the computer 250 is directly connected to the signal recorder 240. In another embodiment (not shown), the computer may be connected to the signal recorder via a communication network, such as a local area network (LAN), a wide area network (WAN) or a global network, such as the Internet. In yet another embodiment (not shown), the computer may contain the signal recorder 240 either as a device or as incorporated functionality. In an alternative embodiment (not shown), the recorder and the computer are not physically connected and the recorded signal data may be provided to the computer on a storage medium.

The computer 250 includes a frequency decomposition module 260, for separating the received EEG signals into different frequency bands, such as the alpha, beta, theta or delta bands. The frequency decomposition module 260 may include instructions for performing the decomposition by implementing a short-time Fourier bandpass filter or through wavelet transformation, both of which preserve the spatio-temporal components of the received signal data.

As is well known, a Fourier filter is a type of filtering function that is based on the frequency components of a signal. The Fourier filter converts a signal into a continuous series of sine waves, each of which is of constant frequency and amplitude and of infinite duration. A bandpass type of Fourier filter works by taking the Fourier transform of the source signal, then cutting off all frequencies above and below a user-specified limit, and then inverse transforming the result. The assumption is made that the frequency components of the signal fall predominantly at low frequencies and those of the noise fall predominantly at high frequencies.

Wavelet transformation converts a signal into a series of wavelets. Through this method, signals processed by wavelet transform can typically be stored more efficiently than ones processed by Fourier transform. In addition, wavelets can also be constructed with rough edges, to better approximate real-world source signals.

The computer 250 also includes a source identifier module 270 which includes instructions to identify a signal source corresponding to each biological signal in a chosen frequency band, according to one embodiment of the invention. The source identifier module 270 identifies the signal sources by performing complex ICA, according to one embodiment. The complex scalp maps resulting from performing complex ICA, can be interpreted in terms of amplitude- and phase-differences between different spatial positions on the scalp produced by the spatio-temporal dynamics of the underlying EEG generators. Alternatively, a constrained complex ICA process may also be used where the independent component (IC) activations remain complex, but the IC scalp maps are required to be real valued, according to one embodiment. It might be of value to constrain the scalp maps to be real-valued, as in standard ICA, simplifying their interpretation and making it possible to further separate the effects induced by wide-band versus band-limited data and by instantaneous (real) versus convolutive (complex) mixing. The source identifier module 270 receives and processes complex frequency-domain data within each spectral band to generate signals, such as a set of complex independent component activation time-courses, that can be monitored by a monitoring module 280 and used, for example, to gain information on brain activity (e.g., by comparing similarities and locating common sources for signal components).

Representations, or component maps, of these activation time courses, showing the strength and/or the polarity of the separated signals may be generated and subsequently visually displayed by a display generation module 290 for monitoring, evaluating and analyzing the received signals. For EEG data, the complex ICA results can be used to generate and display scalp maps corresponding to the complex independent component activation time-courses.

Figure 9:
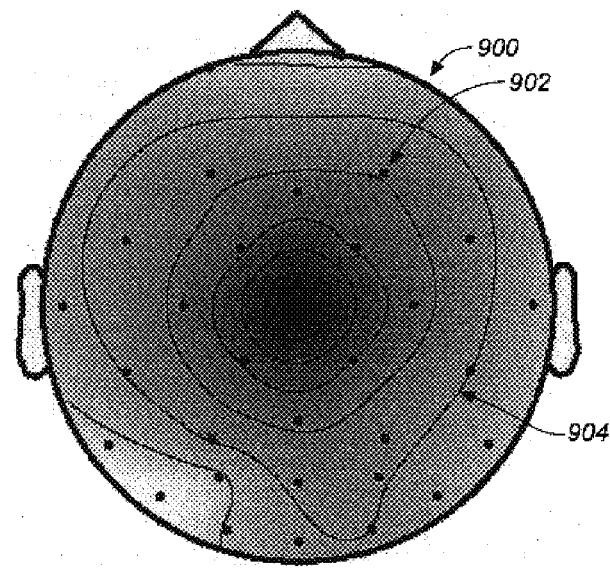
FIG. 9 is an illustration of a representation of signal data, according to one embodiment of the invention.

According to one embodiment, these scalp maps may be represented by images (e.g., the scalp map 900 as shown in FIG. 9) and displayed, depicting signals received from a component activation at an instance of time (e.g., as shown in FIG. 1). In FIG. 9, a scalp map 900 shows multiple electrodes 902, where signals (e.g., voltage signals) are measured and interpolated across the scalp map 900, and characteristic equal-valued lines 904, where the signal are uniform. Conventionally, colors or grayscale levels are used to show signal values (e.g., a darker or more intense image for a higher signal value). According to another embodiment, image representations of scalp maps (e.g., the scalp map 1000 shown in FIG. 10) may be displayed showing a complex frequency domain independent component in one frequency band. The representations of the results may be displayed on the computer 250 using a typical display device. Alternatively, the constrained complex ICA process may be used where the independent component (IC) activations remain complex, but the IC scalp maps are required to be real-valued, to simplify their interpretation or separate the effects induced by the complex ICA process.

Figure 3:
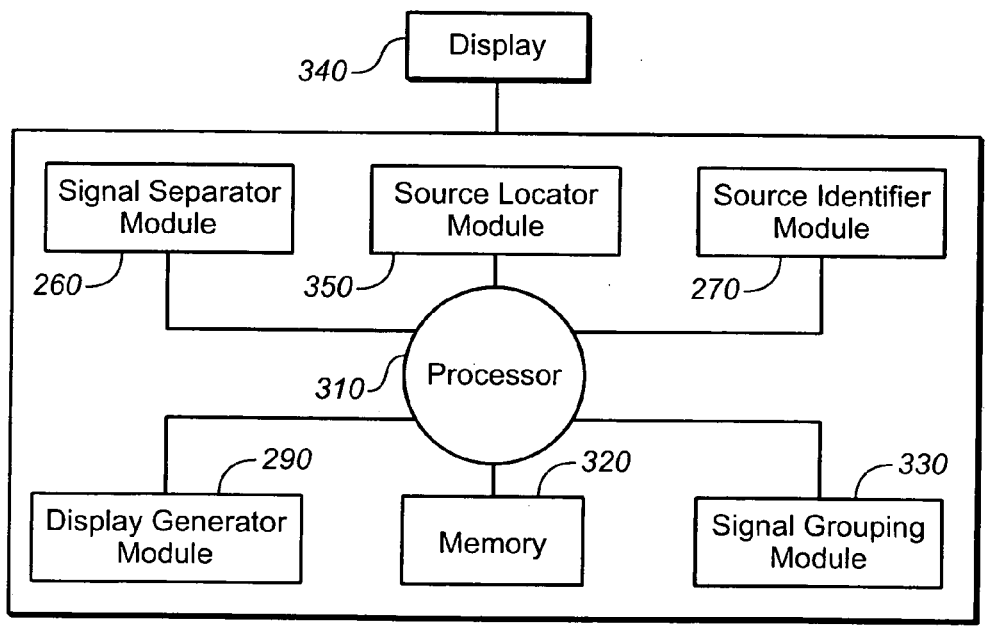
FIG. 3 is a diagram of a computer system, according to one embodiment of the invention.

FIG. 3 shows a block diagram of the computer 250 containing a processor 310, memory 320, and has a display device 340. The computer 250 contains a signal separator module 260 that separates the received mixed signals into signal components within distinct frequency bands. The computer 250 also contains a source identifier module 270, e.g., ICA module that analyzes the signal components within a frequency band, identifying a signal source for the signal components, and generating a time course of activity for the signal source. The source locator module 350 contained in the computer 250 uses the results from source identifier module 270 to determine the source location. Signal grouping module 330 contained in computer 250 compares similarities of signal components in different frequency bands, groups similar signal components, and identifies a common source of the grouped signal components. The source locator module 350 determines the location of the common source of the grouped signal components. The display generation module 290 generates representations of the signal sources and visually displays them on display device 340.

Figure 4:
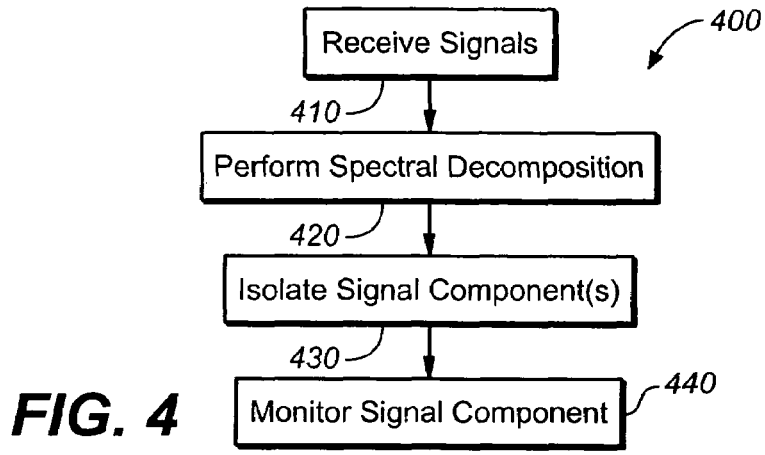
FIG. 4 is a block diagram showing a process of monitoring signals, according to one embodiment of the invention.

The methods described hereinbelow may be performed in accordance with the earlier described processes, according to one embodiment of the invention. FIG. 4 is a block diagram of a method 400 for monitoring signals in a computer system, according to one embodiment of the invention. A plurality of signals are received from a plurality of sensors at a state 410 as recorded data, or real-time or near real-time data. The signals may be biological, such as electroencephalographic, magnetoencephalographic, electromyographic, electrocardiographic, electrogastric, or non-biological signals that may contain spatio-temporal components. Alternatively, the signals may be a set of recorded images, where the images represent a different flow, such as a spatio-temporal flows of different source signals, according to one embodiment. The recorded images can be generated by magnetic resonance imaging, positron emission tomography, or optical imaging. The recorded images may also represent a spread of different sources, or a different growth pattern of different sources, where the source is identifiable by its respective spread signature, or its growth pattern in the image data, according to other embodiments. The recorded images may also represent physical changes in body tissue, or different attributes of physical tissues, according to other embodiments of the invention. According to another embodiment, the recorded images may represent changes of body fluids, including where the body fluid is blood.

After the signals are received at the state 410, the process 400 moves to a state 420 wherein frequency decomposition is used to separate the received signals into signal components within one or more frequency bands. The frequency bands may be selected from frequency bands consisting of delta, theta, alpha, sigma, beta, and gamma, or another defined frequency band. According to one embodiment, Fourier transformation, for example, applying a Fourier bandpass filter, may be used to separate the received signals into one or more frequency bands. According to another embodiment, wavelet transformation, for example, applying a wavelet filter, may be used to separate the received signals into one or more frequency bands. Signal separation by Fourier bandpass filtering or wavelet filtering are signal processing techniques well known in the art. During frequency decomposition, a phase and a magnitude characteristic are calculated for each separate signal component. Separating the received signals into distinct frequency bands may include using a Fourier bandpass filter, according to one embodiment. Alternatively, separating the received signals into distinct frequency bands may include using a wavelet filter, according to another embodiment. Frequency decomposition is described in more detail hereinbelow.

Once the signals are decomposed into separate frequency bands, the process 400 moves to a state 430 wherein the individual signal components are isolated by performing complex ICA, which identifies independent signal components within each frequency band. As a result of performing complex ICA, a time-course of activity of a signal source may be identified for each signal component within the frequency band. During complex ICA, the signal component may be isolated by maximizing the differences between each signal component. A convolutive mixing model can be used with the complex ICA, as previously described, to generate a signal strength calculation. The calculation of the strength of the signal components can include measuring the signal component, for example, measuring the electrical potential of the signal component, with multiple sensors and taking into account, or compensating for, receiving a portion of the signal component at a later time, as further described below and exemplified in Equation (3), according to one embodiment. The convolutive mixing model may also be described in the frequency domain, according to one embodiment. For the frequency domain convolutive model, the strength of the signal component may also be calculated by measuring signals received in one portion of the data, and taking into account, or compensating for, signals received in other portions of the data, as further described below and exemplified in Equation (4) below, according to another embodiment of the invention.

Once independent signal components are identified in the source signals, they may be monitored at a state 440 to evaluate, analyze, or study cortex activity. For example, for EEG or magnetic EEG (MEG) signals, combining information from all the individual independent components in a dense-array EEG data set should allow a kind of dynamic cortex tomography in which the trajectories traversed by the equivalent current dipoles should trace out active portions of cortex. The equivalent dipole shows the polarity of the received signals, importantly recognized as the equivalent dipole 1070 may change for different phase angles, as described below and shown in FIG. 10. If used in a more sophisticated inverse modeling method that begins with projecting activity from the scalp to the cortex, setting a restriction that the active regions of each component at the same frequency should not overlap, a more realistic image of the active regions underlying each component activity can be computed than is possible by current methods. Monitoring the cortical tomography may also be used in medical applications for studying cortical abnormalities of all types. For example, the activity associated with complex components may also differ in power and possibly in component trajectory in subjects with brain abnormalities.

The methods described herein may also be used for EEG monitoring of a cognitive state. For example, the complex ICA techniques described herein may be useful for monitoring alertness or drowsiness, according to one embodiment, which has many applications to the transportation industry and other industries, including the military. In one embodiment, EEG source signals are first separated in order to isolate the delta band signals operating at 0–4 Hz. As is known, these signals correspond to sleep, and are the slowest of the typical EEG signals. In one embodiment, the independent signal components within the delta band are separated to monitored brain activity in different regions of the brain during sleep. Of course, similar experiments could be carried out by analysis of the other frequency bands of EEG signals.

In addition, embodiments of the invention include monitoring EEG signals in a subject during a "surprise" event in order to record the brain activity as the subject experiences their reaction to the surprise event. Of course, other types of activities, such as the degree of confidence with which a subject makes a decision, such as pushing a button, and the degree of warning, such as provoking alarm, displeasure, or fear, the subject associates with an event can be recorded. By studying these types of reactions, and separating independent signal components from within the various frequency bands, one might realize commonalities in brain activity for each of the aforementioned activities. For example, use of this information could be applied for job monitoring and also in lie detection.

Complex ICA decomposition may also allow more realistic modeling of the flow of blood and blood oxygen in the brain linked to various types of cognitive activity, as in functional magnetic resonance imaging (fMRI data). To do this, the method may be switched into the complex spatial Fourier domain. Abnormalities in blood flow, such as associated with stroke and other brain blood flow anomalies, as well as in coordinated activity, across a few seconds, in separate brain areas, may be distinguished. Another application is to diffusion tensor imaging (DTI) of fibre tracts in the brain, as these are increasingly being shown to be markers of cognitive deficits.

More generally, the methods of this invention may be applied to signal domains in which the relevant information is contained in a subset of frequency bands, and which are recorded after liner mixing. For example, these signal domains may include fluid, oceanographic, or weather imaging, stack market data or genetic data.

Figure 5:
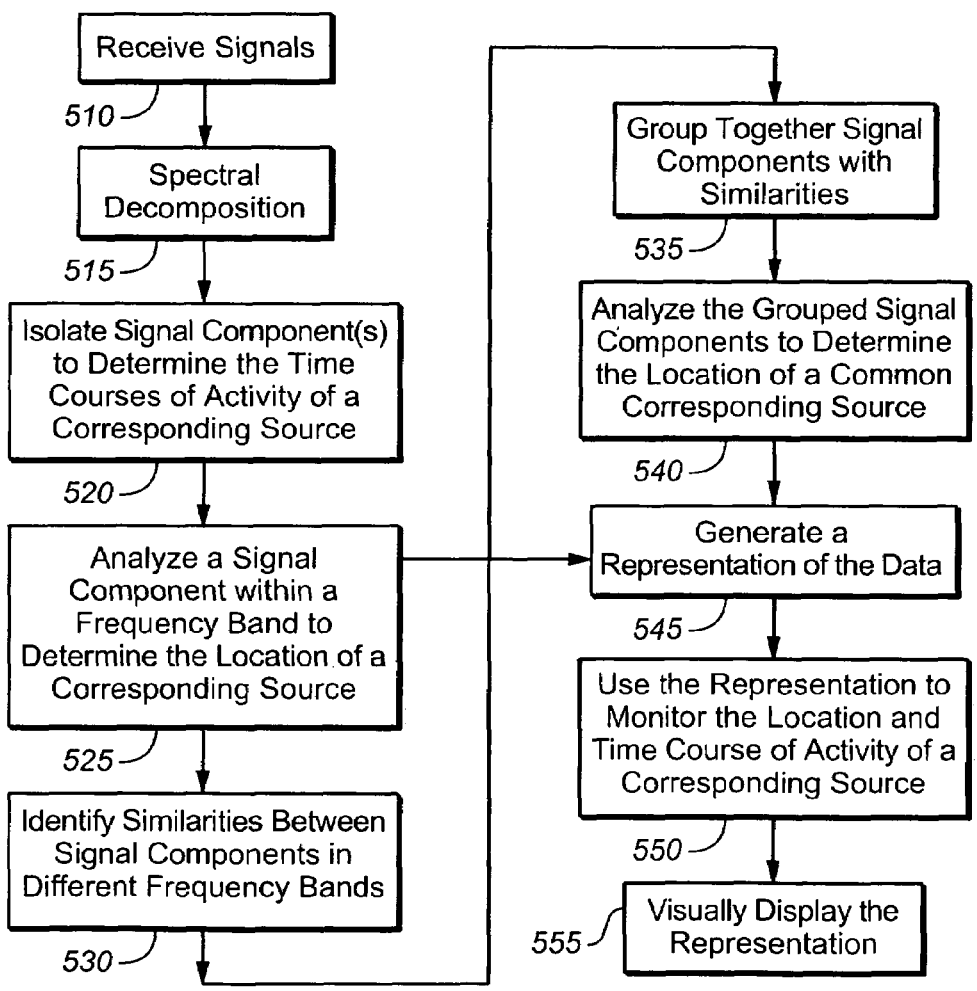
FIG. 5 is a block diagram showing a process of monitoring signals, according to one embodiment of the invention.

FIG. 5 shows a block diagram of a method 500 for monitoring signals, according to one embodiment of the invention. A plurality of signals are received at a state 510 from a plurality of sensors, as recorded data, or real-time or near real-time data, and may be of many different types, as previously described. Frequency decomposition is performed at a state 515 to separate the signals into signal components within one or more distinct frequency bands. The signal components are isolated at a state 520 by performing complex ICA, according to one embodiment of the invention, and time courses of activity are identified for a source corresponding to a signal component.

Using the results from complex ICA, a signal component is analyzed at a state 525 to determine the location of a corresponding source, using backprojection and localization, as previously described, according to one embodiment.

A representation of the source location may be generated at a state 545 by depicting the signals received at the multiple locations from the corresponding source, according to one embodiment.

Figure 10:
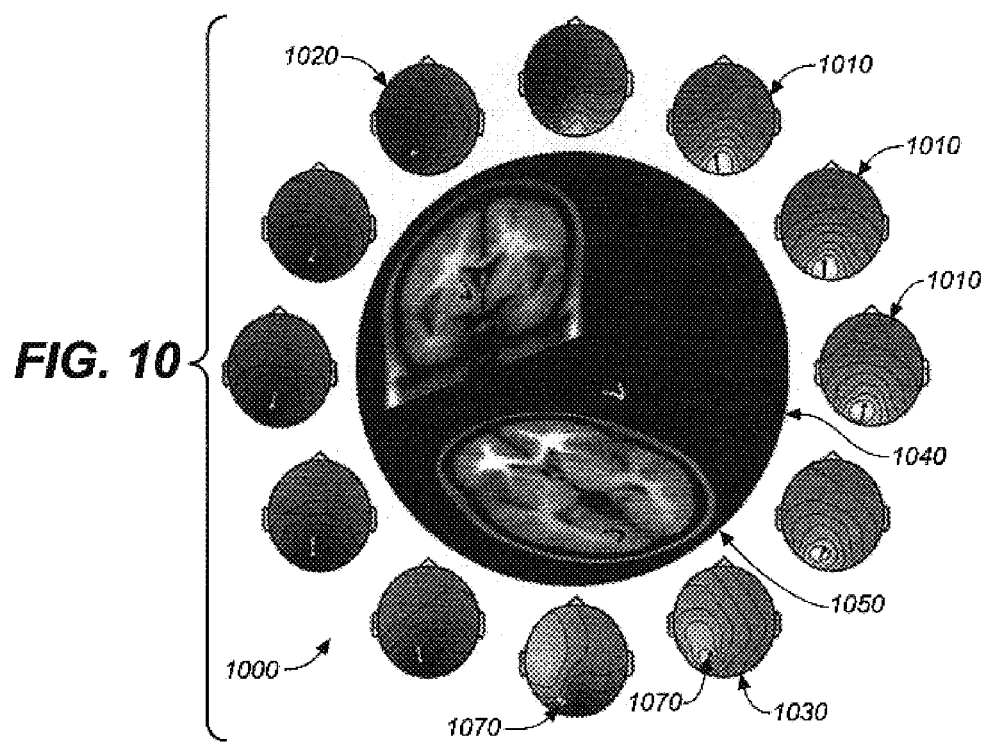
FIG. 10 is an illustration of a representation of signal data, according to one embodiment of the invention.

FIG. 10 shows an example of a generated representation of a source location of a complex frequency-domain independent component in the alpha band, in accordance with one embodiment. The twelve maps 1010 show the progression (clockwise) of potential across the scalp projected by the component process during each 10 Hz (100-ms) cycle. Mathematically, these are real projections of the complex component map onto different phase angles, where each of the twelve maps 1010 is a representation of a different phase angle. Superimposed on the two-dimensional maps is a three-dimensional view of the equivalent current dipole 1070 for each map, as determined by individual dipole fitting using Brain Electrical Source Analysis (BESA) or other tools known to those skilled in the art of EEG analysis. Residual variance of the dipole models, using all 32 channels, is less than 3% for all but the near-zero magnitude maps 1020, 1030. The central panel 1040 shows the three-dimensional trajectory 1050 of the equivalent current dipole, plus its two-dimensional projections 1060 on the coronal and axial views of an average brain image. The component models an alpha frequency oscillation in which the center of successive positive and negative wave fronts travel along a convex 2–3 cm arc in the left occipital cortex.

Referring back to FIG. 5, after signal components are isolated within a frequency band, the similarities of signal components in different frequency bands may be analyzed at a state 530 and corresponding components in distinct frequency bands that likely represent activity of the same physiological source may be identified at a state 535. Identifying similarities of signal components in the different frequency bands may include comparing the strength of the identified signal components, for example, comparing the signal components to see if they both show a strong signal strength or a weak signal strength at the same time, according to one embodiment, where a high correlation of the strengths of compared signal components indicates similarity between the signal components. Identifying similarities of signal components in the different frequency bands may include comparing the distance between component maps, where the distance may be based on the euclidian distance of the complex vectors representing the two component maps, according to one embodiment. Identifying and grouping, i.e., clustering, the groups of similar components across frequencies based on the distance between component maps and the distance between component activations are described in further detail below, and shown in Equations (30) and (32), respectively. The grouped components are then analyzed at a state 540 to determine the location of a common source corresponding to the grouped components, and representations depicting the signals received at the multiple locations or the corresponding source may be generated at a state 545. According to one embodiment, the location of the source is determined by the backprojection and localization processes described hereinbelow.

Representations, such as those shown in FIG. 9 or FIG. 10, may be used to monitor the locations and time courses of activity at a state 550, thereby allowing further evaluation of the signal data including visually displaying the representation 555. According to one embodiment, the representations may depict the strength of the signals received, as shown in FIG. 10, by representing the strength of the signal by different levels of shading or color. In another embodiment, the representations may depict the polarity of the signals received, as also shown in FIG. 10, by the current dipole 1070 color (e.g., white or black) or its direction. To further facilitate monitoring and evaluation of the signal data, the representations may be visually displayed. For example, the twelve maps 1010 in FIG. 10 may be displayed on a computer display. The representations also may be displayed as a sequence of images, such as is shown by the smaller images 1010 surrounding a center image in FIG. 10, according to one embodiment. Alternatively, the sequence of images may be shown on a display device, and maybe shown in rapid succession to form a "movie" of the monitored activity.

Hereinbelow are described embodiments of frequency decomposition, the convolution mixing model, and a variant of infomax complex ICA. Also described are embodiments for a variant of the infomax complex ICA constrained to real scalp maps, visualization of complex activations and maps, and measures for assessing the quality of the signal separation. Further described are embodiments for measuring similarities between independent components in distinct frequency bands, and methods for comparing real time domain and complex frequency-domain ICA results. The embodiments herein describe one or more ways the invention may be practiced, however; these descriptions should not be interpreted as limiting the invention to only the embodiments described. Instead, the invention should be construed in accordance with the appended claims and any equivalents thereof.

Frequency Decomposition

To perform frequency decomposition, a function may be defined for the measured signals $x_i(t)$, where $i=1, \ldots, M$ denotes electrodes, according to one embodiment of the invention. The frequency time-frequency representations of the measured signals are computed as $$x_i(T, f) = \sum_{\tau} x_i(T + \tau) b_f(\tau), \qquad (1)$$

where f denotes center frequency, and $b_f(\tau)$ the basis function which extracts the frequency band f from the time-domain signal. The basis function is centered at time T. Hence, data of size [channels i×times t] is transformed into data of size [channels i×times T×frequencies f].

According to one embodiment, frequency decomposition may be performed by means of the short-time Fourier transformation such that $b_f(\tau)$ is given by $$b_f(\tau) = h(\tau) e^{-i 2\pi f \tau / 2K}, \qquad (2)$$

$h(\tau)$ being a windowing function (for example a hanning window) with finite support in the interval $\tau=-K, \ldots, K-1$, and 2K denoting the window length. Correspondingly, the frequency index acquires values $f=0, \ldots, K$. Since the product of time- and frequency-resolution is bounded from below by 0.5, the chosen windowing function and window length give limited frequency-domain resolution. Alternatively, a wavelet filter may be used for separating the received signals into defined frequency bands, according to one embodiment. Filtering signals with a wavelet filter is well known in the art and, accordingly, will not be described herein.

Convolutive Mixing Model

One way to allow the effective sources to exhibit more complex dynamics is to assume a convolutive mixing model. By using a convolutive mixing model together with complex ICA, single effective sources with traveling-wave characteristics may be identified from the received EEG signals, as such a model allows for detecting and separating patterns of spatial propagation of source signals. Convolutive mixing in the time-domain is equivalent to multiplicative mixing in the frequency-domain with generally distinct complex valued mixing coefficients in different frequency bands. EEG activity has distinctive characteristics in different frequency bands which may be associated with different physiological processes, or sources. To account for these frequency specific characteristics, a frequency specific mixing model can be used for each frequency band, according to one embodiment.

The convolutive mixing model may be described in the time domain or the frequency domain. To describe the convolutive mixing model in the time domain first, let $s_j(t)$, $j=1, \ldots, N$ be the N source signals, $x_i(t)$, $i=1, \ldots, M$ be the mixed signals received by M sensors, and $a_{ij}(t)$ the influence of source j on sensor i. If source j is switched on briefly at time $t=0$ with strength $s_j(0)$, then the signal induced at the sensors by that source at consecutive times t is given by $s_j(0)a_{ij}(t)$. Hence, the sequence $a_{ij}(t)$ is a direct result of the source traveling along its associated trajectory within the brain. If source is active continuously (and not only briefly at time $t=0$), then the corresponding signal induced at the sensors is given by the convolution of $s_j(t)$ with $a_{ij}(t)$. If not only a single source j is active, but all sources $j=1, \ldots, N$ are active simultaneously, then the signal recorded at the sensors corresponds to the sum of all the individual convolutions, i.e., the full convolutive mixing system in the time-domain is given by $$x_i(t) = \sum_j^N \sum_t a_{ij}(t)s_j(t - t). \quad (3)$$

The convolution mixing model may also be described in the frequency-domain. For each frequency band f, the signals $x(T,f)=[x_1(T,f), \ldots, x_M(T,f)]^T$ are assumed to be generated from independent sources $s(T,f)=[s_1(T,f), \ldots, s_N(T,f)]^T$ by multiplication with a frequency-specific mixing matrix $A(f)$ thus, $$x(T,f)=A(f)s(T,f), \quad (4)$$

with rank $(A(f))=N$. Noise in the received signals may be assumed to be negligible, according to one embodiment. The embodiment described herein assumes square-mixing, that is, where the number of signals is equal to the number of independent sources (M=N). However, these methods are also applicable to the case where the number of signals is greater than the number of sources (M>N). The estimates $u(T,f)$ of the sources are obtained from the sensor signals by multiplication with frequency-specific separating matrices $W(f)$, $$u(T,f)=W(f)x(T,f). \quad (5)$$

Complex ICA

Figure 6:
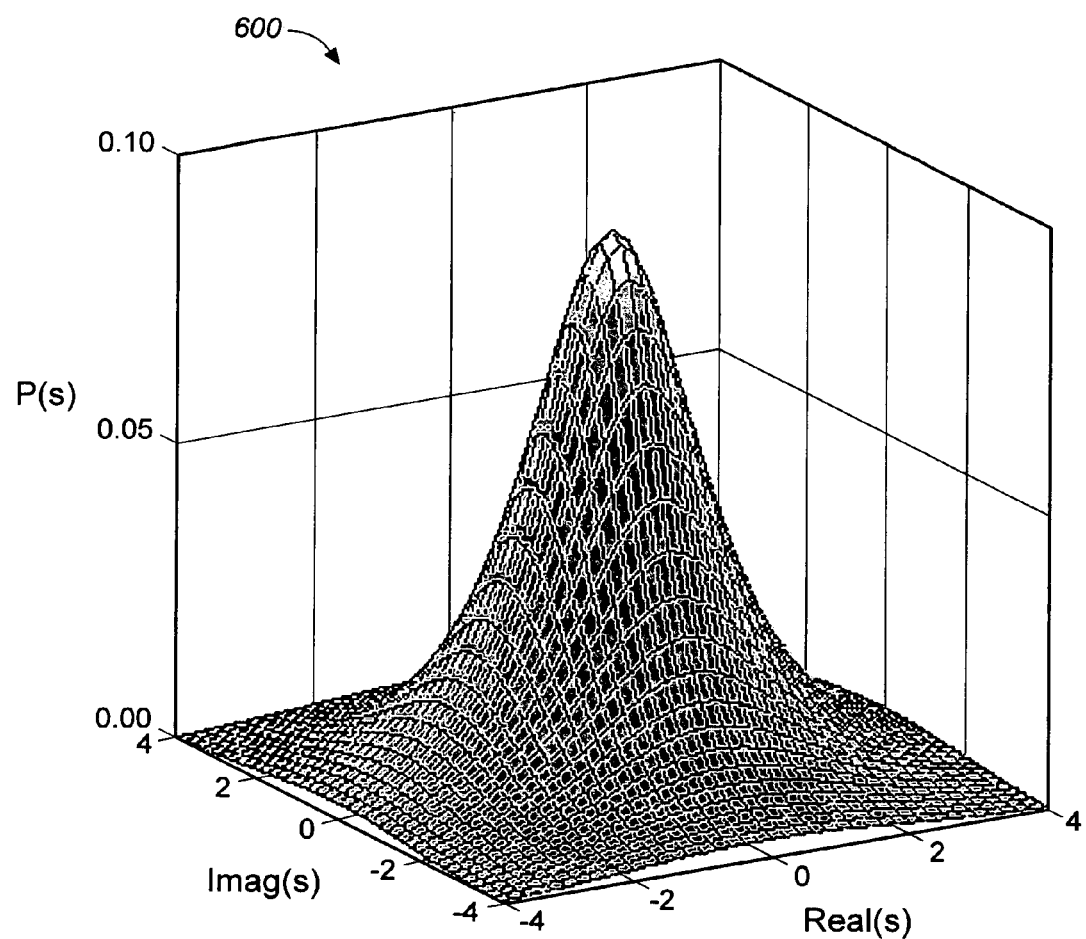
FIG. 6 is a graph illustrating the circular symmetric super-Gaussian probability density function P(s) of a complex source.
Figure 7:
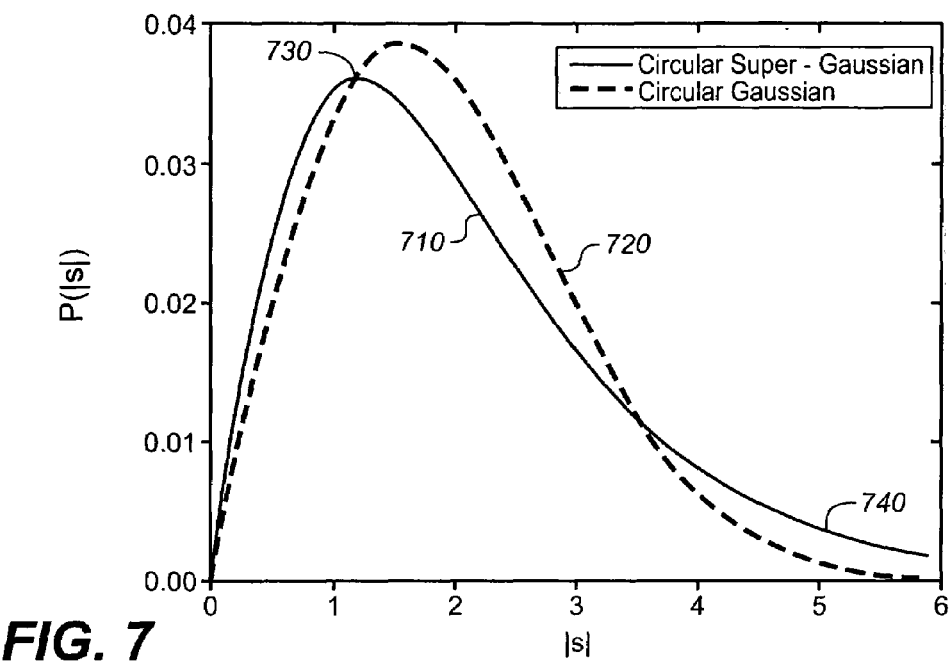
FIG. 7 is a graph showing the distribution $P_{|s|}(|s|)$ of the magnitude $|s|$ versus the corresponding distribution for a two-dimensional Gaussian distribution of the same variance, according to one embodiment of the invention.

For the complex ICA process, the sources $s_j(T,f)$ are modeled as complex random variables with a circular symmetric, super-Gaussian probability density function $P_s(s)$, according to one embodiment. The property of circular symmetry of the distribution is a direct result of the window-centers T being chosen independently of the signal. Hence, $P_s(s)$ may depend only on the magnitude $|s|$ of s and can be written as $$P_s(s)=g(|s|) \quad (6)$$

with the function $g(\cdot)$ defined over the real line. The assumed two-dimensional distribution $P_s(s)$ over the complex plane is illustrated in FIG. 6, which shows the circular symmetric super-Gaussian probability density function $P(s)$ 600 of the complex sources s. The non-Gaussianity of the distribution can be seen by plotting the corresponding distribution $P_{|s|}(|s|)$ of the magnitude $|s|$ 710 (depicted by a solid line) versus the corresponding distribution for a two-dimensional Gaussian distribution of the same variance 720 (depicted by a dashed line) as shown in FIG. 7. The latter distribution 720 is the well-known Rayleigh distribution. The super-Gaussian source distribution is characterized by its stronger peak 730 at small magnitudes and its longer, high-magnitude tail 740.

The complex ICA separating matrix $W(f)$ is obtained by maximizing the log-likelihood $L(W(f))$ of the measured signals $x(T,f)$ given $W(f)$, which in terms of the source distribution $P_s$ is $$L(W(f))=<\log P_s(x(T,f)|W(f))>_T=\log \det (W(f))+<\log P_s(W(f)x(T,f))>_T, \quad (7)$$

where $<\cdot>_T$ denotes expectation computed as the sample average over T, according to one embodiment. Maximization may be performed by complex gradient ascent on the likelihood-surface. For example, (i,j)-element $\delta w_{ij}(f)$ of the gradient matrix $\nabla W(f)$ may be defined as $$\delta w_{ij}(f) = \left(\frac{\partial}{\partial \Re w_{ij}(f)} + i\frac{\partial}{\partial \Im w_{ij}(f)}\right)L(W(f)), \quad (8)$$

where $\partial/\partial \Re w_{ij}(f)$ and $\partial/\partial \Im w_{ij}(f)$ denote differentiation with respect to the real and imaginary parts of matrix element $w_{ij}(f)=[W(f)]_{ij}$, respectively. This results in the gradient $$\nabla W(f)=(I-<v(T,f)u(T,f)^H>_T)W^{-H}(f), \quad (9)$$

however, faster convergence may be achieved by using the complex extension of the natural gradient $$\tilde{\nabla} W(f)=\nabla W(f)W(f)^H W(f)=(I-<v(T,f)u(T,f)^H>_T)W(f), \quad (10)$$

where $$v(T,f)=[v_1(T,f), \ldots, v_N(T,f)]^T, \quad (11)$$

$$v_i(T,f) = \text{sign}(u_i(T,f))\frac{g'(|u_i(T,f)|)}{g(|u_i(T,f)|)}, \quad (12)$$

$$\text{sign}(z) = \begin{cases} 0 & \text{if } z=0, \\ z/|z| & \text{if } z \neq 0. \end{cases} \quad (13)$$

Here, I denotes the identity matrix, $g'(\cdot)$ is the first derivative of function $g(\cdot)$, and H denotes complex conjugation and transposition.

For the choice $$\frac{g'(x)}{g(x)} = \frac{1-e^{-x}}{1+e^{-x}} \quad (14)$$

a complex generalization of the standard logistic infomax ICA learning rule is obtained. In the case of purely real-valued data, the learning rule for complex data reduces to the infomax ICA learning rule for real signals.

Due to the circular symmetry of $P_s$, the log-likelihood $L(W(f))$ is invariant with respect to the multiplication of any row $w_i(f)$ of $W(f)$ with an arbitrary unit-norm complex number $c_i(f)$, $|c_i(f)|=1$. This parallels the sign-ambiguity of real ICA process using symmetric non-linearities. However, since the circular symmetry allows for continuous invariance transformations (in contrast to the discrete sign-flip operation), detection of convergence is hindered. Therefore, one can constrain the diagonal of $\tilde{\nabla}W(f)$ by projecting it to the real line, thereby reducing the invariance to a sign-flip ambiguity.

The independent component decomposition based on Equation (10) is performed separately for each frequency band f, yielding in total $N(K+1)$ complex independent component activation time-courses $u_i(T,f)$ and $N(K+1)$ complex scalp maps $a_j(f)$, where $a_j(f)$, denotes the j-th column of the estimated mixing matrix $A(f)=W^{-1}(f)$.

Complex ICA Constrained to Real Scalp Maps

The complex scalp maps $a_j(f)$ may be interpreted in terms of amplitude- and phase-differences between different spatial positions on the scalp produced by the spatio-temporal dynamics of the underlying EEG generators. Signal evaluations or monitoring may also be done by constraining the scalp maps to be real-valued as in standard ICA. Together with simpler interpretation, this approach has the advantage of making it possible to further separate the effects induced by wide-band versus band-limited data and by instantaneous (real) versus convolutive (complex) mixing. Signal superposition by means of different real-valued mixing matrices in distinct frequency bands corresponds to convolutive mixing in the time-domain using symmetric filters.

To constrain the process' solution to real scalp maps, the initial estimate of $W(f)$ is chosen to be real (typically the identity matrix), and the gradient Equation (10) is projected to the real plane, resulting in the constrained gradient $$\tilde{\nabla}\Re W(f) = \Re(\tilde{\nabla}W(f)), \quad (15)$$

with $\Re$ denoting the real part. While the corresponding scalp maps $a_j(f)$ are real, the separated IC activations $u(T,f)$ remain complex.

Equation (15) differs from applying standard infomax ICA to the real-parts of $u(T,f)$ in that its underlying source model, Equation (6), is still based on a distribution over the complex plane. As a result, the product $v(T,f)u(T,f)^H$ in the right hand side of Equation (15) is evaluated using complex multiplication. In principle, performing complex ICA to derive real-valued component maps may be more accurate than performing real ICA on concatenated real and imaginary parts of band-limited time-frequency transformations, as the circular symmetric complex distribution assumed by complex ICA may be more accurate than the (real) cross-product of real and imaginary part distributions used in the real frequency ICA decomposition method.

Visualizing Complex IC Activations and Maps

Complex independent component activations $u_i(T,f)$ may be conveniently visualized by separately plotting their power and phase. The power of the complex independent component activations may be determined by their squared amplitude. To simplify the visual impression of the phase data, the effect of phase advances locked to the carrier frequency are "unwrapped" by complex demodulation, multiplying the IC activations with $\exp(-i2\pi fT/2K)$. This yields complex signals in the frequency band centered at 0 Hz, and the phase angles may then be plotted.

For multi-trial data, this results in two ERP(event related potential)-image plots showing event-related power and phase at each frequency f. For a visual presentation, the trials may be grayscale coded after sorting in order of ascending response time followed by smoothing. According to one embodiment, smoothing is performed using a 30-trial wide rectangular window. Response time in each trial may be plotted superimposed on the data. The time-courses of mean event-related power and intertrial coherence may then be computed from the multi-trial data by averaging data from identical event-related time-windows across trials.

To best visualize the complex component maps, the invariance of the source model, shown in Equation (6), with respect to rotation around the origin may be taken into account. Therefore, for each complex map $a_j(f)=[a_{ij}(f), \ldots, a_{Mj}(f)]^T$ any rotated version $c_j(f)a_j(f)$ thereof constitutes an equivalent map, with $c_j(f)$ an arbitrary unit-norm complex number. For visualization we plot real-part, imaginary-part, magnitude and phase values of the equivalent map $\hat{a}_j(f)=c_j(f)a_j(f)$ for which the sum of the imaginary parts $\Im$ vanishes and the sum of the real parts $\Re$ is positive, i.e., $$\sum_i \Im(\hat{a}_{ij}(f)) = \Im\left(c_j(f)\sum_i a_{ij}(f)\right) = 0 \text{ and } \sum_i \Re(\hat{a}_{ij}(f)) > 0 \quad (16)$$

$$\Rightarrow c_j(f) = \frac{\sum_i a_{ij}^*(f)}{\left|\sum_i a_{ij}(f)\right|}. \quad (17)$$

A complex map $\hat{a}_j(f)$ whose elements $\hat{a}_{ij}(f)$ have negligible (near zero) imaginary part for all $i=1, \ldots, M$ indicates that the corresponding EEG process may represent activity of a highly synchronized generator ensemble. A non-negligible imaginary part is equivalent to phase-differences between distinct scalp electrode positions, which may be elicited by more complex spatio-temporal dynamics of the corresponding EEG process, for example, spatial propagation of EEG activity.

Degree of Separation

To quantify the degree of signal separation attained, the second- and fourth-order measures of statistical dependency may be computed.

Second-order correlations are taken into account by computing, for each frequency f the mean $\rho(f)$ of the absolute values of correlation-coefficients $\rho_{ij}(f)$ for all different components pairs $i \neq j$:

$$\rho(f) = \frac{1}{N(N-1)} \sum_{i \neq j} \rho_{ij}(f), \quad (18)$$

where the correlation-coefficients are defined as $$\rho_{ij}(f) = \left| \frac{\langle u_i(T,f) u_j^*(t,f) \rangle_T - \mu_i(f) \mu_j^*(f)}{\sigma_i(f) \sigma_j(f)} \right|, \quad (19)$$

$$\mu_i(f) = \langle u_i(T,f) \rangle_T, \quad (20)$$

$$\sigma_i(f) = \sqrt{\langle |u_i(T,f) - \mu_i(f)|^2 \rangle_T}. \quad (21)$$

Here $\rho_{ij}(f)$ vanishes for uncorrelated signals and acquires its maximum value (i.e., one) only when signals $u_i(T,f)$ and $u_j(T,f)$ are proportional. Since the measured signals $x(T,f)$ are complex, except at 0 Hz and at the Nyquist frequency, complete decorrelation may in general only be achieved by the fully-complex ICA process, shown in Equation (10), whereas the real-map constrained-complex ICA process, shown in Equation (15), and time-domain ICA will generally exhibit non-zero values of $\rho(f)$.

Second-order decorrelation is generally not sufficient condition for statistical independence. Therefore, higher-order statistical dependencies may also be evaluated, at least in part, by computing the analog quantity $\rho'(f)$ of the time-course of squared amplitudes $|u_i(T,f)|^2$:

$$\rho'(f) = \frac{1}{N(N-1)} \sum_{i \neq j} \rho'_{ij}(f), \text{ where} \quad (22)$$

$$\rho'_{ij}(f) = \left| \frac{\langle |u_i(T,f)|^2 |u_j(t,f)|^2 \rangle_T - u'_i(f) u'_j(f)}{\sigma'_i(f) \sigma'_j(f)} \right|, \quad (23)$$

$$u'_i(f) = \langle |u_i(T,f)|^2 \rangle_T, \quad (24)$$

$$\sigma'_i(f) = \sqrt{\langle (|u_i(T,f)|^2 - u'_j(f))^2 \rangle_T}. \quad (25)$$

Equation (23) measures statistical dependency of fourth order. It can be interpreted as a modified and normalized variant of a fourth-order cross-cumulant. Its value is zero for independent signals, non-zero for signals exhibiting correlated fluctuations in signal power, and maximum value (i.e., one) for signals with proportional squared-amplitude time-courses.

Source Localization from Complex ICA Data

Once complex ICA has been performed on the data, cortical flow patterns, corresponding to the received EEG signals, may be located by using backprojection and localization methods. These methods may use the notation described hereinafter, according to one embodiment of the invention. M: the number of measured (i.e., mixed) signals; N the number of separated signals (sources); $x(T,f) = [x_1(T,f), \ldots, x_M(T,f)]^T$: the measured signals; $W(f)$: the complex separating matrix for frequency band f; $A(f) = W^{-1}(f)$: the complex mixing matrix for frequency band f; $a_j(f_1)$: the j-th column of matrix $A(f)$; $a_j(f)$ is also referred to as the complex independent component map associated with component j at frequency f, $u(T,f) = [u_1(T,f), \ldots, u_N(T,f)]^T$: the separated signals, i.e., the complex component activation functions that are obtained as $u(T,f) = W(f) x(T,f)$.

The backprojection method is a standard technique in the area of signal processing via independent component analysis, according to one embodiment. While the measured signals are "real" physical quantities in the sense that they are actually recorded with a physical device (e.g., scalp electrodes in the case of EEG signals) and measured in some physical unit (e.g., Volts for scalp potentials), the independent component activations lack the direct interpretation in terms of physical quantities. Therefore, backprojection is used to compute the contribution of one (or several) independent components to the recorded signals. For EEG signals, it corresponds to finding which part of the measured electrode voltages is elicited by some independent component(s). To do this, the standard backprojection method may be extended to the case where sources and mixing system are complex.

For an independent component j for some frequency f with its associated time-course $u_j(T,f)$ and a map $a_j(T,f)$, the calculation of the corresponding backprojection of this component may depend on the frequency decomposition of the signals. If the frequency decomposition of the time-domain signals $x(t)$ has been computed with consecutive window-centers shifted by a single sample, then the frequency-domain sources are also given at every sample time. Hence, time-indices t (time-domain) and T (frequency-domain) cover the same range, up to some points at the edges. In this case, the back-projected time-domain signals $v(t)$ are computed as $$v(t) = v_{j,i}(t) = \Re(u_j(t,f) a_j(f)), \quad (26)$$

where $\Re(x)$ denotes the real part of complex number x.

If the window-shift of the frequency decomposition is larger than one sample, the back-projected frequency-domain signals are computed as $$v_{ij}(T) = \Re(u_j(T,f) a_j(f)), \quad (27)$$

and have to be transformed back to the time-domain using standard techniques of digital signal processing, such as, inverse Fourier transformation and overlap-add reconstruction, yielding time-domain backprojections $v(t)$.

According to one embodiment, for backprojection of multiple components, let component activations and maps be given for components $j_1, j_2, \ldots$ at corresponding frequencies $f_1, f_2, \ldots$. The aim is to obtain a single time-domain backprojection which reflects the cumulative contribution of these components to the measured signals. Backprojection is first done separately for each pair $(j_1, f_1), (j_2, f_2), \ldots$, yielding time-domain backprojections $v_{j_1, f_1}(t), v_{j_2, f_2}(t), \ldots$. These are then summed to obtain the combined backprojection $$v(t) = v_{j_1, f_1}(t) + v_{j_2, f_2}(t) + \ldots. \quad (28)$$

Once the backprojection step has been performed, the source locations can be obtained using EEG source localization methods. For each time-point $t=1,2,\ldots$, the source location corresponding to the back projected map $v(t)$ at that time t is computed, resulting in a series of source localizations which can then be visualized, such as with a moving source movie. Source localization can be performed with standard methods, such as using equivalent dipole localization or distributed source models.

Corresponding Components in Distinct Frequency Bands

The complex frequency-domain ICA process described above produces separate sets of independent components for distinct and comparably narrow frequency bands. Activity in some underlying EEG source domains might exhibit strictly narrow-band characteristics. However, generator activity may also take place in a broader frequency range comprising contiguous or disconnected frequency bands. Narrow-band ICA analysis does not take into account such links between bands, but separates the data into independent components ordered arbitrarily (e.g., by band-limited power) in each band. Therefore, components that may account for activity within a single underlying EEG generator may be captured by components in multiple bands (with possibly distinct component numbers). To obtain a full picture of the underlying EEG processes, it is desirable to identify and group together those components in different bands that likely represent activity of the same physiological source.

Described hereinbelow are methods for identifying and clustering groups of similar components across frequencies, according to one embodiment of the invention. The methods may be based on appropriate measures of distance between pairs of component maps or component activations, respectively. Matching component pairs may then be identified using a standard optimal-assignment procedure.

Distance Between Component Maps

The definition of the distance between component maps is based on the euclidian distance $|a_i(f_1) - a_j(f_2)|$ of the complex vectors $a_i(f_1)$ and $a_j(f_2)$ representing two maps. Since euclidian distance is not invariant with respect to arbitrary rescaling of the maps, it should be normalized. The multiplication of one map with an arbitrary unit-norm complex number $c, |c|=1$, also alters the euclidian distance, although it results in an equivalent map. Therefore, the map distance $d_{map}(i, f_1, j, f_2)$ of maps $a_i(f_1)$ and $a_j(f_2)$ may be defined as the rescaled minimal euclidian distance between the normalized maps, $$d_{map}(i, f_1, j, f_2) = \frac{1}{\sqrt{2}} \min_c \left| c \frac{a_i(f_1)}{|a_i(f_1)|} - \frac{a_j(f_2)}{|a_j(f_2)|} \right|, |c| = 1, \quad (29)$$

which may be written equivalently in terms of their inner-product as $$d_{map}(i, f_1, j, f_2) = \min_c \left( \sqrt{1 - \left( \frac{\mathcal{R}((ca_i^H(f_1)a_j(f_2)))}{|a_i(f_1)||a_j(f_2)|} \right)^2} \right) = \left( \sqrt{1 - \left( \frac{|a_i^H(f_1)a_j(f_2)|}{|a_i(f_1)||a_j(f_2)|} \right)^2} \right). \quad (30)$$

The map distance measure attains its maximum value (i.e., one) for orthogonal maps and its minimum value (i.e., zero) only for equivalent maps.

Distance Between Component Activations

The distance between complex component activations may be defined based on the correlation of signal-power time-courses at different frequencies. Between IC activations $u_i(T,f_1)$ and $u_j(T,f_2)$ at frequencies $f_1$ and $f_2$, respectively, the component activation distance $d_{act}(i,f_1,j,f_2)$ may be defined as $$d_{act}(i,f_1,j,f_2) = 1 - \rho'_{ij}(f_1 f_2), \quad (31)$$

where, analogously to Equation (22), $\rho'_{ij}(f_1 f_2)$ denotes the correlation-coefficient of the squared-amplitude time-courses $|u_i(T,f_1)|^2$ and $|u_j(T,f_2)|^2$, $$\rho'_{ij}(f_1 f_2) = \left| \frac{\langle |u_i(T, f_1)|^2 |u_j(t, f_2)|^2 \rangle_T - u'_i(f_1); u'_j(f_2)}{\sigma'_i(f_1)\sigma'_j(f_2)} \right|, \quad (32)$$

with $\mu'_i(f)$ and $\sigma'_i(f)$ defined according to Equations (24) and (25), respectively. By this measure, completely independent signals have a maximal distance value (i.e., one), whereas signals with highly correlated fluctuations in signal power have distance near the minimum value (i.e., zero). Related changes in signal power in different frequency bands may be exhibited by EEG generators with activity in both bands, since modulation of generator activity—induced, e.g., by experimental events or common modulatory processes—may result in synchronous amplitude changes, in the same or different direction in the participating bands.

Assigning Best-Matching Component Pairs

Based on the distance measures described for component maps and component activations, the set of pairs of best-matching components is defined to be that which minimizes the average distance between the pairs.

For example, consider a given pair of frequencies $(f_1, f_2)$ and a chosen distance measure $d(i,f_1,j,f_2)$ (either map distance $d_{map}$ or activation distance $d_{act}$). Assigning best-matching component pairs is equivalent to finding the permutation $\pi(i)$, $i=1, \ldots, N$, that assigns component i at frequency $f_1$ to component $j=\pi(i)$ at frequency $f_2$ such that the mean distance across all pairs, $$\sum_i d(i, f_1, \pi(i), f_2)/N,$$

is minimized:

$$\pi(\cdot) = \arg \min_{\pi(\cdot)} \sum_i d(i, f_1, \pi(i), f_2), \quad (33)$$

$$D(f_1, f_2) = \min_{\pi(\cdot)} \frac{1}{N} \sum_i d(i, f_1, \pi(i), f_2). \quad (34)$$

Determining $\pi(i)$ given the matrix of distances $d(i,f_1,j,f_2)$ between all pairs (ij) is known as the 'assignment problem' and it can be solved using well-known processes (e.g., the so-called Hungarian method).

The minimal mean distance $D(f_1,f_2)$ is a global measure of the distance between the sets of components at frequencies $f_1$ and $f_2$. For equal frequencies, $f_1=f_2$, $D(f_1,f_2)$ always attains its minimum value (i.e., zero), and the permutation becomes the identity, $\pi(i)=i$. If the components at frequency $f_1$ are identical to the components at frequency $f_2$, but occur in a different order, then $D(f_1,f_2)$ is also zero and $\pi(i)$ corresponds to the permutation of order. If some components are identical at both frequencies, whereas the remaining components exhibit maximum distance to all other components, then $D(f_1,f_2)$ corresponds to the fraction of non-identical components. For the realistic case of few components being reproduced exactly across frequencies and many components matching similar but not identical components at other frequencies, $D(f_1,f_2)$ attains values between zero and one, indicating the degree of average similarity of the best-matching component pairs.

Time-Domain ICA

Separation results from time-domain ICA may be analyzed using similar methods as those presented for the analysis of frequency-domain ICA. Time-domain infomax ICA is applied to the time-domain signals $x_i(t)$, resulting in a single separating matrix W. The corresponding components maps are given by the columns $a_j$ of the mixing matrix $A=W^{-1}$. Frequency-specific unmixed signals may be obtained by applying W to the frequency transforms of the sources, yielding complex separated signals u(T,f)=Wx(T,f), from which one can compute the measures for the quality of separation (cf. Equations (18), (22)). Distances between time-domain and frequency-domain components are obtained based on the methods presented for corresponding components in distinct frequency bands. The distance $d_{map}$(i,j,f) between time-domain ICA maps $a_i$, and frequency-domain ICA maps $a'_j(f)$ is computed analogously to Equation (29). Similarly, IC activations obtained with time-domain and frequency-domain ICA are compared by computing the distance $d_{act}$(i,j,f) in analogy to Equation (31). The best-matching component pairs in the different frequency bands may then be grouped together by the methods previously disclosed for assigning best-matching component pairs.

Experimental Results

In this section, results are presented from a visual spatial selective attention experiment wherein the subject attended one out of five indicated locations on a screen while fixating a central cross, and was asked to respond by a button press as quickly as possible each time a target stimulus appeared in the attended location. Included in the analysis were 582 trials from target stimulus epochs collected from one subject. Each epoch was 1 s long, beginning at 100 ms before stimulus onset at t=0 ms.

The data were recorded from 31 EEG electrodes (each referred to the right mastoid) at a sampling rate of 256 Hz and decomposed into 101 equidistantly spaced frequency bands with center frequencies from 0.0 Hz (DC) to 50.0 Hz in 0.5-Hz steps. Decomposition was performed by short-time discrete Fourier transformation with a hanning window of length 50 samples, corresponding to a frequency resolution of 5.12 Hz (defined as half width at half maximum), and a window shift of 1 sample between successive analysis windows. This yielded 207 short-time spectra for each trial derived from analysis windows centered at times between 1.6 ms and 806.3 ms following stimulus presentations in 3.9 ms steps.

To decompose the data into independent components, the 582 trials were concatenated, resulting for each frequency band, f=0, . . . , 101, and channel, i=1, . . . , 31, in frames T=1, . . . , 207×582=120474. No pre-training sphering of the data was performed. The separating matrix W(f) was initialized with the identity matrix for all frequency bands. The logistic non-linearity Equation (14) was used followed by computation of the gradients, Equation (10) and Equation (15), respectively, at each iteration step from 10 randomly chosen data points, and the learning rate of the gradient ascent procedure was successively lowered. Optimization of W(f) was halted when the total weight-change induced by one sweep through the whole data was smaller than $10^{-6}$ relative to the Frobenius norm of the weight-matrix.

The dataset was decomposed using both the fully-complex, Equation (10), and the real-map constrained-complex, Equation (15), processes. For comparison, the same dataset was also decomposed using time-domain infomax ICA applied to the time-domain data $x_i(t)$; the obtained single real separating matrix was then applied to the frequency-domain data x(T,f) as described above for Time-domain ICA.

Kurtosis

Kurtosis may be used to test the assumption of super-Gaussian source distributions, by assessing deviations from a Gaussian distribution. Kurtosis estimates were computed for frequency-domain data as $$\mathrm{kurt}(z) = <|z|^4> - 2(<|z|^2>)^2 - |<zz>|^2 \quad (35)$$

assuming a zero-mean, unit-variance complex random variable z. The Kurtosis kurt(z) vanishes for a Gaussian distribution and attains positive and negative values for super- and sub-Gaussian distributions, respectively.

Kurtosis of the frequency-domain electrode signals $x_i(T,f)$ was computed individually for each channel i at every frequency f, yielding 31×101=3131 kurtosis estimates, each based on all 120474 complex data frames. All of the 3131 channel-frequency kurtosis estimates showed a super-Gaussian distribution with minimum 0.02, maximum 23.45 and median 0.43. A histogram of the kurtosis values is displayed in FIG. 8, which shows histograms for estimated kurtosis of complex frequency-domain electrode signals 810. Each histogram is based on 3131 kurtosis estimates, with 44 bins of width 0.05 in the interval from 0 to 3.

Figure 8:
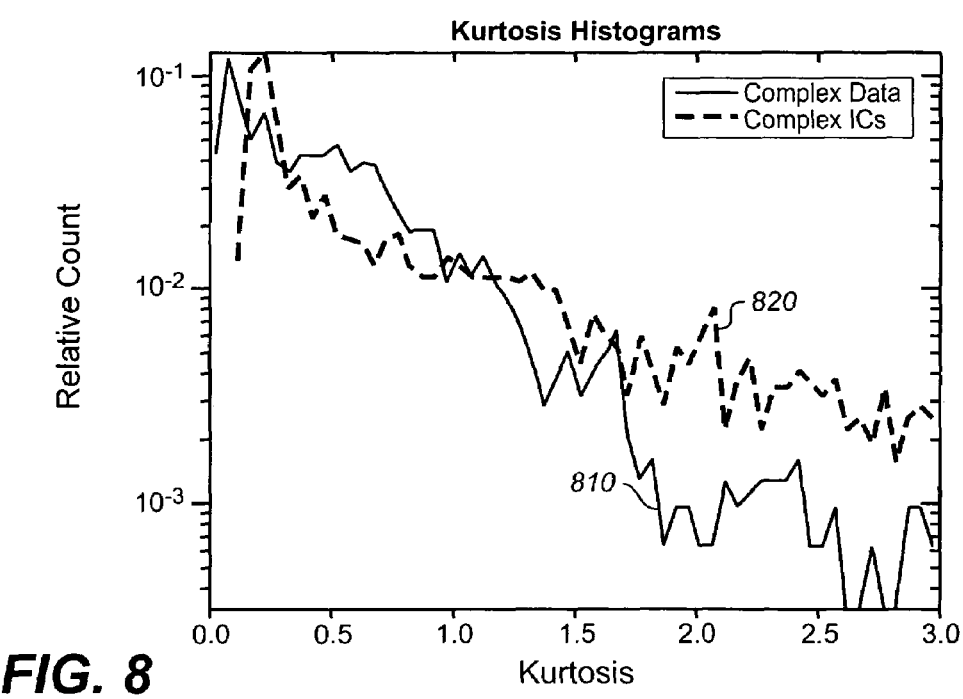
FIG. 8 is a graph showing the estimated kurtosis of complex frequency electrode signals and independent component activations, according to one embodiment of the invention.

Analogously, the same number of kurtosis estimates for the IC activations $u_j(T,f)$ obtained with the fully-complex ICA process were computed. The median kurtosis increased to 0.55 and only super-Gaussian distributions in the range [0.10, 386.79] were found. The corresponding histogram for IC activations 820 is shown in FIG. 8.

These results support the given choice for the source model and suggest that only a small advantage might be expected by allowing the source distributions to include sub-Gaussian sources. Although use of sub-Gaussian sources is not discussed in any detail here, alternative embodiments may employ sub-Gaussian sources, which may have advantages in some operational settings.

Degree of Separation

Figure 11A:
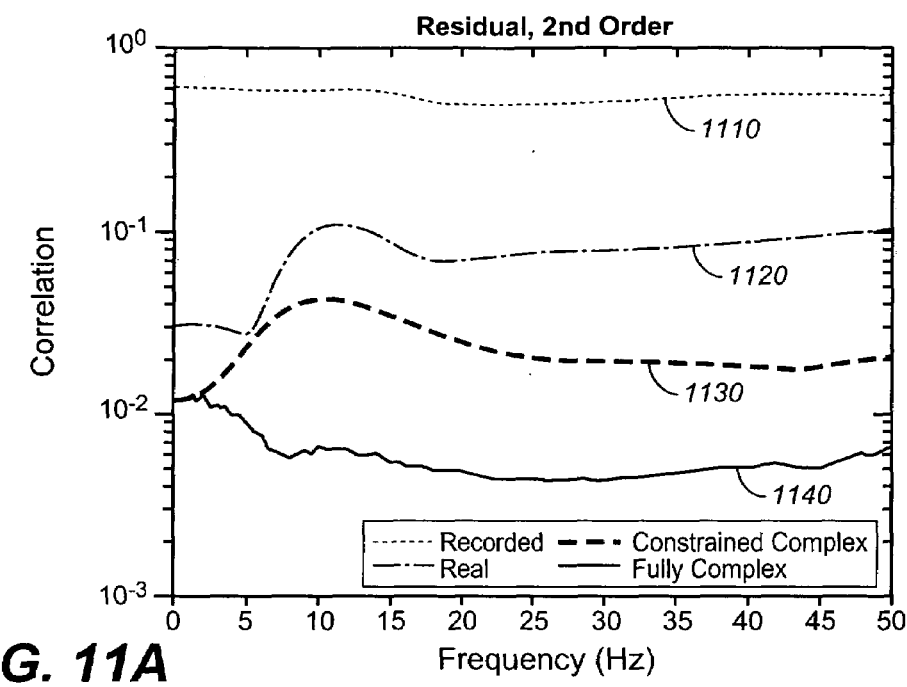
FIG. 11A is a graph illustrating residual statistical dependencies evaluated using second-order measures, according to one embodiment of the invention.
Figure 11B:
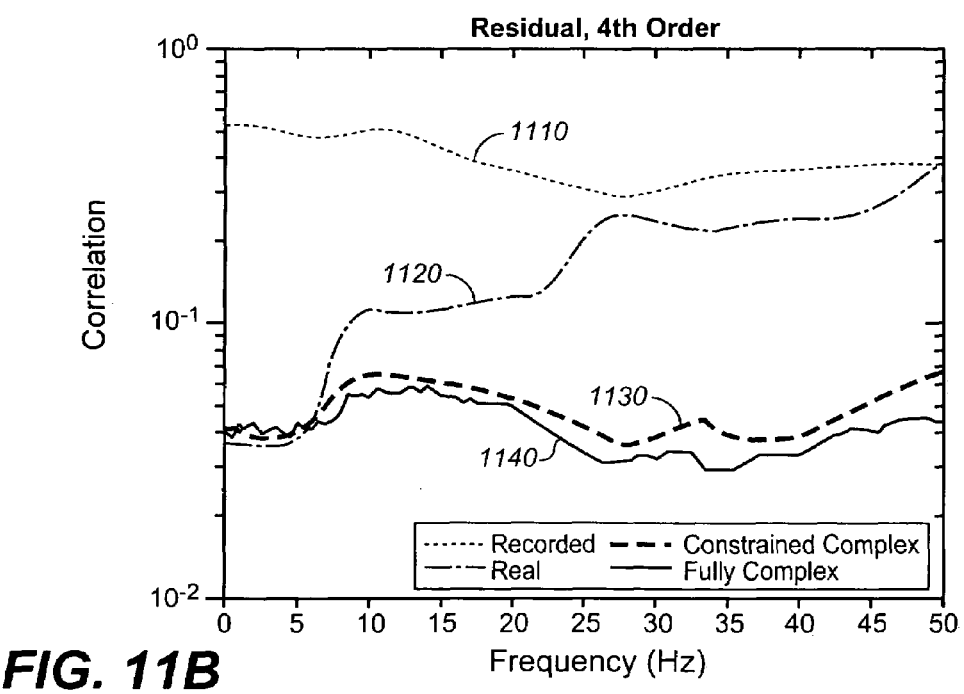
FIG. 11B is a graph illustrating residual statistical dependencies evaluated using fourth-order measures, according to one embodiment of the invention.

To assess the degree of separation achieved by the different ICA processes, the residual statistical dependencies were computed using the second-order, Equation (18) and fourth-order, Equation (22), statistics described above. Results are displayed in FIG. 10 for the recorded electrode signals and for the separations into sources obtained from real time-domain infomax ICA, real-map constrained-complex and fully-complex frequency-domain ICA. Residual statistical dependencies were evaluated using second-order, shown in FIG. 11A, and fourth-order, shown in FIG. 11B, measures at frequency bands between 0 Hz and 50 Hz. Residuals for the recorded electrode signals 1110 (dotted), signal separation obtained from real time-domain infomax ICA 1120 (dash-dotted), real-map constrained-complex frequency-domain ICA 1130 (dashed), and fully-complex frequency-domain ICA 1140 (solid). For both measures and all frequencies, fully-complex ICA achieved the lowest levels of residual dependencies. Real-map constrained results exhibited comparably higher residuals, and time-domain infomax ICA still higher levels.

The residual second-order correlations exhibited by fully-complex ICA were, with the exception of very low frequencies, about one order of magnitude lower than those attained by time-domain ICA, and below half of those achieved by real-map constrained-complex ICA. This result may largely be explained by the higher number of degrees of freedom of the complex ICA process that model the superposition within each frequency band with a different mixing matrix, whereas time-domain ICA uses a single matrix for all frequencies. Fully-complex ICA achieved the lowest levels of residual correlation since it is the only process that models superposition using a different complex matrix for every frequency, which in general is necessary to decorrelate complex input signals. In the 0-Hz frequency band, the frequency-domain electrode signals are real, which explains the similar performance of the real-map constrained- and fully-complex process at the lower end of the frequency range.

The residual fourth-order correlations showed a smaller difference between the real-map constrained and fully-complex ICA process, the latter exhibiting slightly lower residual dependencies for all but very low frequencies. There was almost no difference in fourth-order correlations between the three process in the range from 0 Hz to approximately 6 Hz, which may be due to the small imaginary parts and high power of the signals in this range. Between about 6 Hz and 50 Hz, the residual fourth-order correlations of time-domain ICA showed large fluctuations—near 27 Hz and 50 Hz component independence was close to that of the recorded signals.

These findings indicate that additional degrees of freedom of the frequency-domain convolutive mixing model (compared to the instantaneous mixing model) enable it to produce components with a higher degree of signal separation. The assumption of a fully-complex mixing model appears to be supported by the resulting lower residual dependencies.

Distance Between Component Maps

Figure 12:
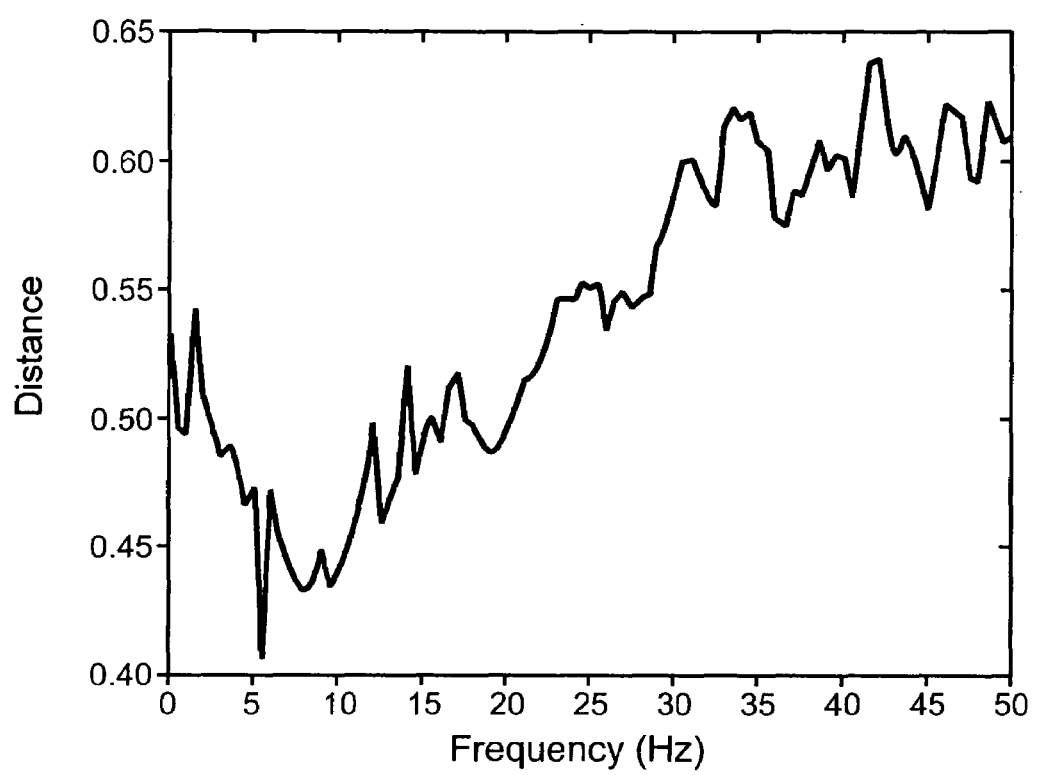
FIG. 12 illustrates mean distance between component maps, according to one embodiment of the invention.

The time-domain ICA compared and real-map constrained-complex ICA were further compared by computing, for every frequency f=1, . . . , 101, the distance $d_{map}(i,j,f)$ between the i-th component map of time-domain ICA and the j-th component map of complex ICA at frequency f. Best-matching component maps were assigned for each f using the assignment method described above, yielding a minimal mean distance D(f), analogous to Equation (34). FIG. 12 shows the mean distance between the component maps obtained by time-domain infomax ICA and best-matching frequency-specific component maps of real-map constrained-complex ICA, where the abscissa is the frequency of frequency-domain component, and the ordinate is the mean distance to time-domain ICA map.

Across all frequencies, the distance between component maps obtained by time-domain ICA and by constrained-complex frequency-domain ICA is at least 0.4. Largest distances are exhibited at frequencies of 30 Hz or higher, while the maps show closest resemblance around a minimum in the 5-Hz to 10-Hz range.

Distance Between Component Activations

Figure 13:
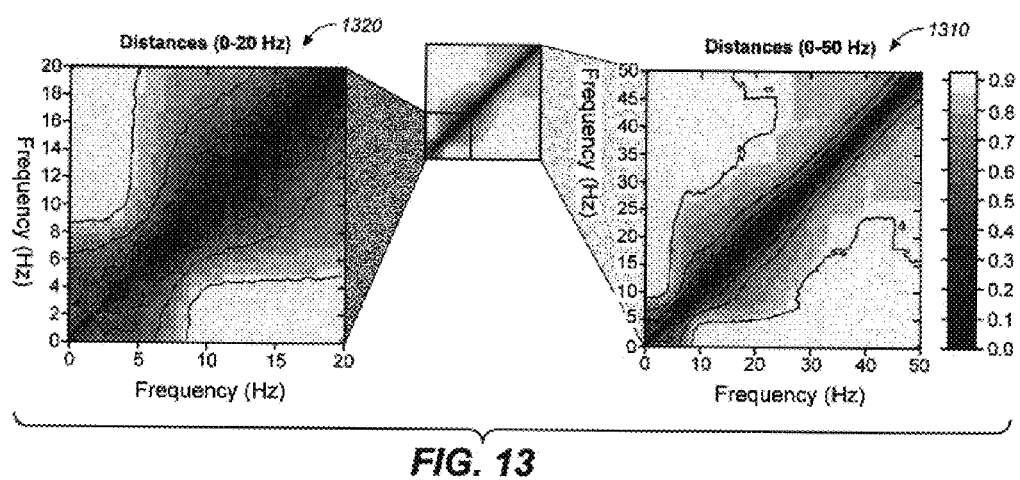
FIG. 13 illustrates minimal mean distances between component activations, according to one embodiment of the invention.

Distances between component activation time-courses $u_j(T,f_1)$ and $u_i(T,f_2)$ were computed for the full-complex ICA separation according to Equation (31) for all possible combinations of $(i,f_1,j,f_2)$. Best-matching components were assigned for each pair of frequencies $(f_1,f_2)$ using the method presented above, yielding one minimal mean distance $D_{act}(f_1,f2)$ for every frequency pair. The distances between all frequency pairs are represented visually 1310 in FIG. 13 (right panel). FIG. 13 shows the minimal mean distances $D_{act}(f_1,f_2)$ computed from component activation functions obtained with the fully-complex ICA process in 101 frequency bands of width 5.12 Hz, spaced equidistantly between 0 Hz and 50 Hz in 0.5-Hz increments. FIG. 13 shows the distances for all best matching component pairs of different frequencies 1310, and the enlarged view of the 0-Hz to 20-Hz range 1320.

The distance matrix exhibits a structure that may be said to separate the frequency range into several clusters. Low-frequencies in the delta range (0–4 Hz) form a cluster with only weak interactions with components at other frequencies. Two less pronounced clusters are visible, one ranging from about 5 Hz to about 25 Hz and another from about 25 Hz to at least 50 Hz, both of which exhibit component activation similarities across a wide frequency range.

An enlarged view of the 0-Hz to 20-Hz range 1320 is displayed in FIG. 13. The data indicates that the 5-Hz to 20-Hz range is further subdivided into at least two sub-clusters, the first of which extends from about 5 Hz to about 8 Hz, i.e., spans mainly the theta (4-Hz to 8-Hz) range. A second cluster extends from about 12 Hz upwards and incorporates beta (13-Hz to 30-Hz) frequencies. An area of weaker across-frequency interactions may be formed by frequencies from about 9 Hz to about 12 Hz, corresponding to the alpha (8-Hz to 13-Hz) range. The comparably lower level of between-frequency interactions in this range could be accounted for by the narrow frequency peaks that are characteristic of alpha activity.

Though these clusters were obtained with a purely data-driven method, they appear to match remarkably well frequency ranges which have long been distinguished by EEG researchers, indicating the complex frequency-domain ICA method may extract components with physiological relevance from EEG data.

Examples of Maps and Activations

A large number of independent component maps and activations were obtained for the different frequency bands. We here show one set of components whose central-midline projections are similar to EEG activity associated with orienting to novel stimuli. The response of these components to stimulus presentation is most marked in the 5-Hz band. FIGS. 14A–C, 15A–C, and 16A–C illustrate differences between the real infomax, real-map constrained-complex infomax and fully-complex infomax ICs.

Figure 14A:
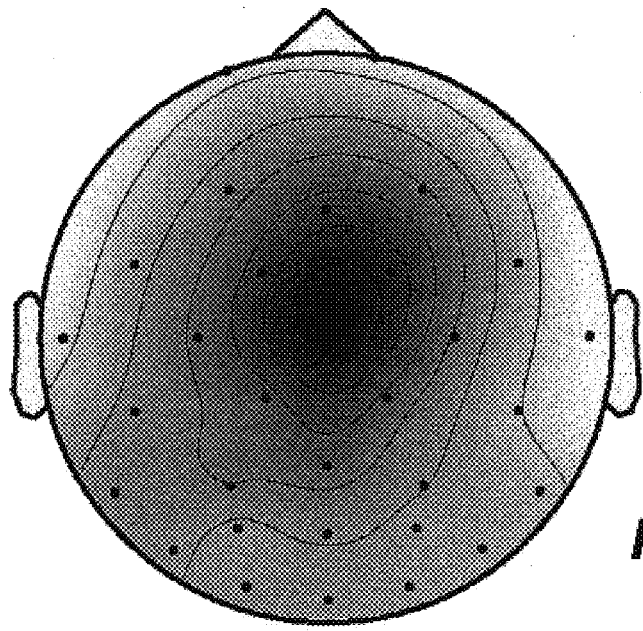
FIG. 14A is a representation of a scalp map, according to one embodiment of the invention.
Figure 14B:
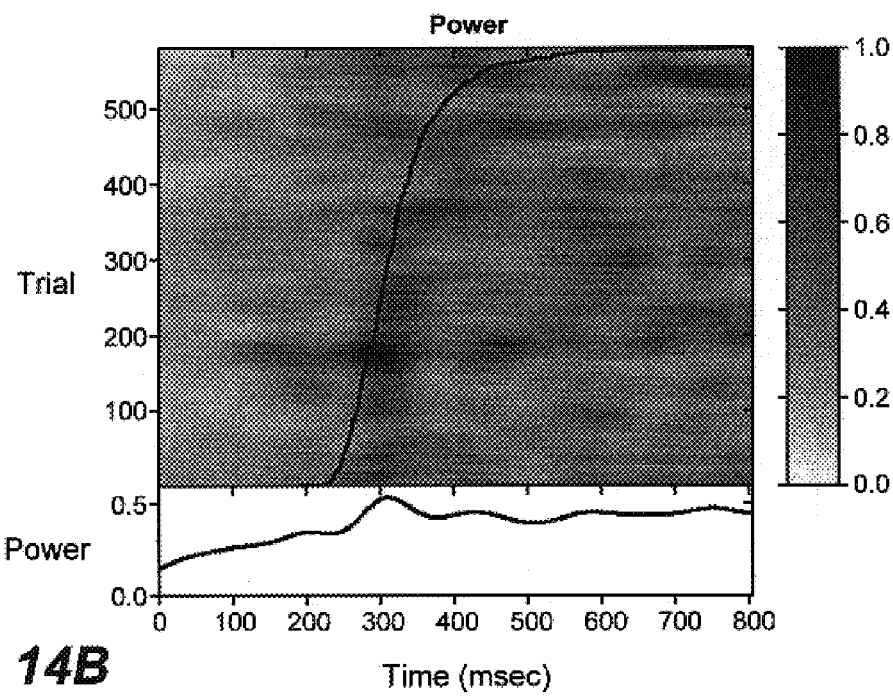
FIG. 14B is a representation of an ERP-image, according to one embodiment of the invention.
Figure 14C:
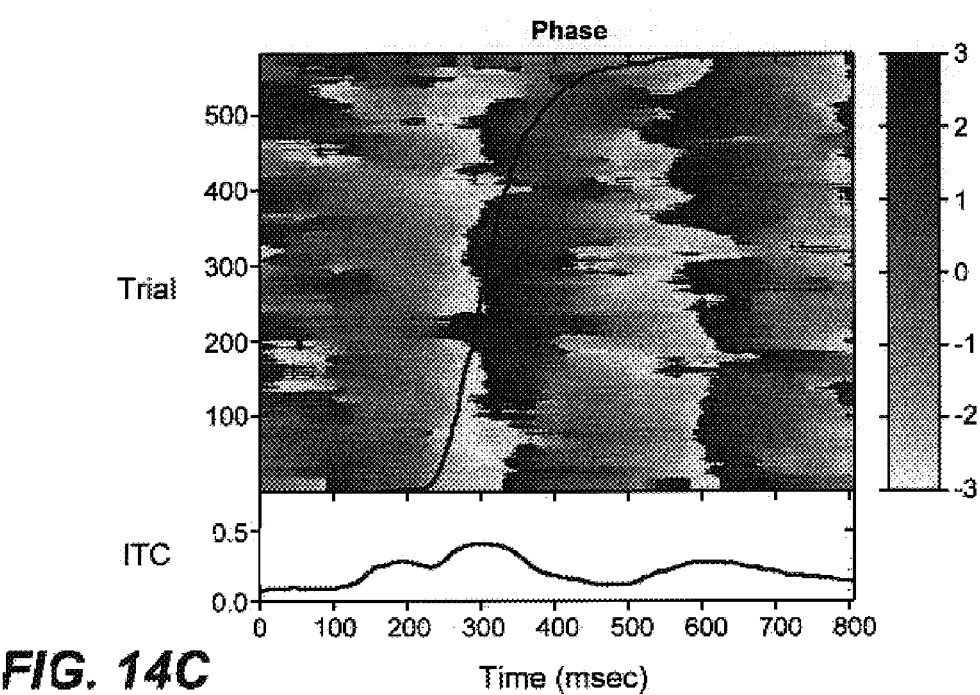
FIG. 14C is a representation of an ERP-image, according to one embodiment of the invention.

FIGS. 14A–C show the independent component at 5 Hz obtained from standard time-domain infomax ICA. FIG. 14A shows a scalp map of this data. FIG. 14B shows a ERP-image of 5-Hz power, and the lower panel shows mean time-courses of event-related 5-Hz power. FIG. 14C shows an ERP-image of complex demodulated 5-Hz phase, with the lower panel displaying the 5-Hz intertrial coherence (ITC). FIG. 14B shows a clear increase in power near the median response time at about 300 ms, and FIG. 14C shows a strong mean phase resetting which is visible near 300 ms as a phase wrap (from $-\pi$ to $\pi$) and as a peak in the ITC.

Figure 15A:
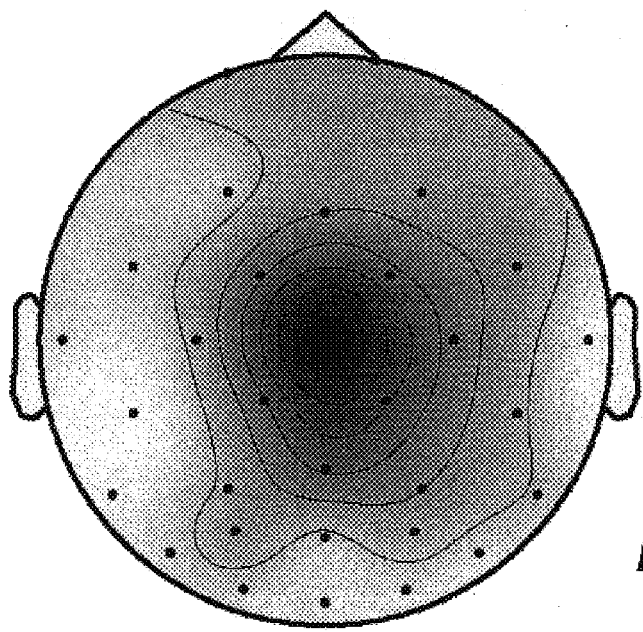
FIG. 15A is a representation of a scalp map, according to one embodiment of the invention.
Figure 15B:
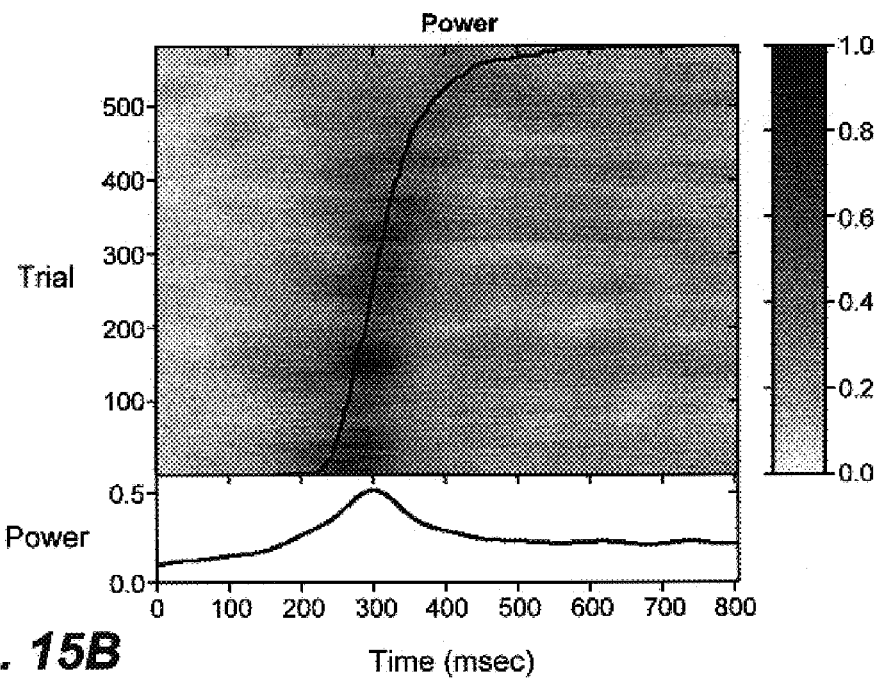
FIG. 15B is a representation of an ERP-image, according to one embodiment of the invention.
Figure 15C:
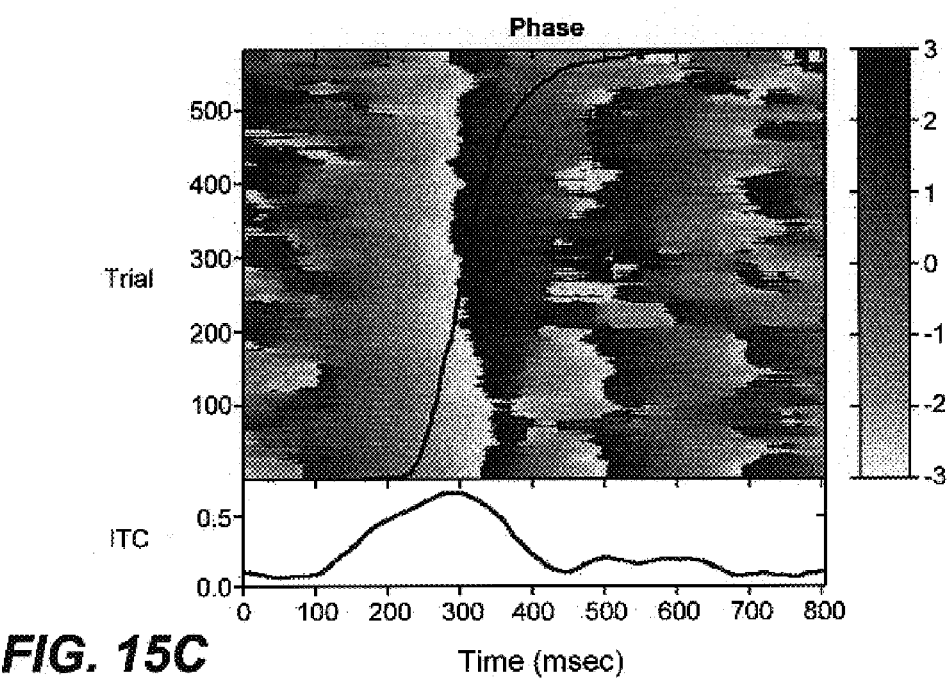
FIG. 15C is a representation of an ERP-image, according to one embodiment of the invention.

FIGS. 15A–C show the independent component at 5 Hz obtained from real-map constrained-complex frequency-domain ICA. FIG. 15A shows the scalp map. FIG. 15B shows the ERP-image of 5-Hz power. FIG. 15C shows the ERP-image of complex-demodulated 5-Hz phase. The data set used in FIGS. 14A–C was used here. The component map 15A shares the spatial focus of maximum scalp projection with the time-domain IC map shown in FIG. 14A, but the spatial extent of the projection appears different. Comparing the complex activation time-courses between FIGS. 14A–C and 15A–C, one notes that the real-map constrained-complex IC shows a stronger response-locked power increase near 300 ms which is also more closely linked to the response time, as shown in FIG. 15B, and shows a more consistent phase-resetting near 300 ms after stimulus presentation, as shown in FIG. 15C. This indicates that frequency domain ICA may reflect subject behavior and underlying brain processes more faithfully than time-domain ICA.

Figure 16A:
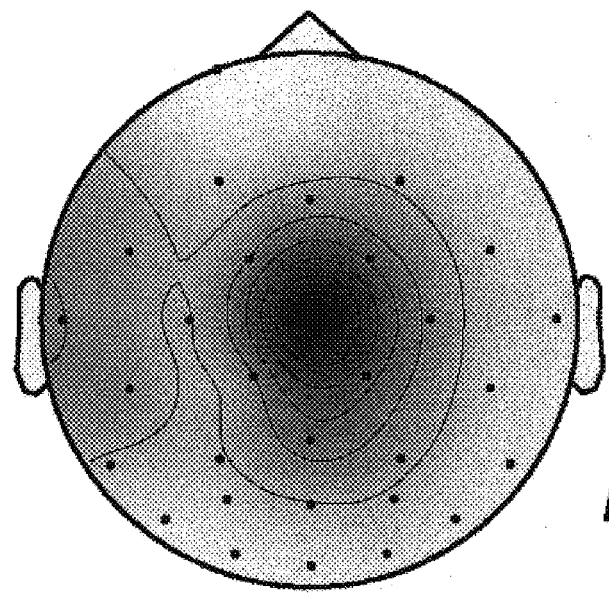
FIG. 16A is a representation of a scalp map, according to one embodiment of the invention.
Figure 16B:
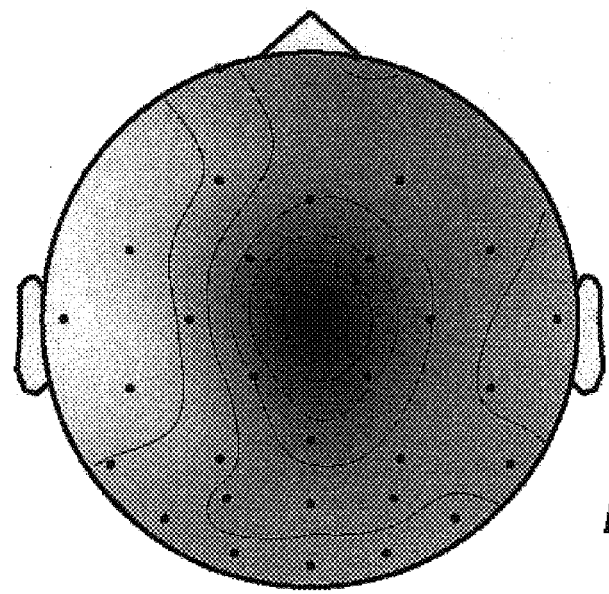
FIG. 16B is a representation of a scalp map, according to one embodiment of the invention.
Figure 16C:
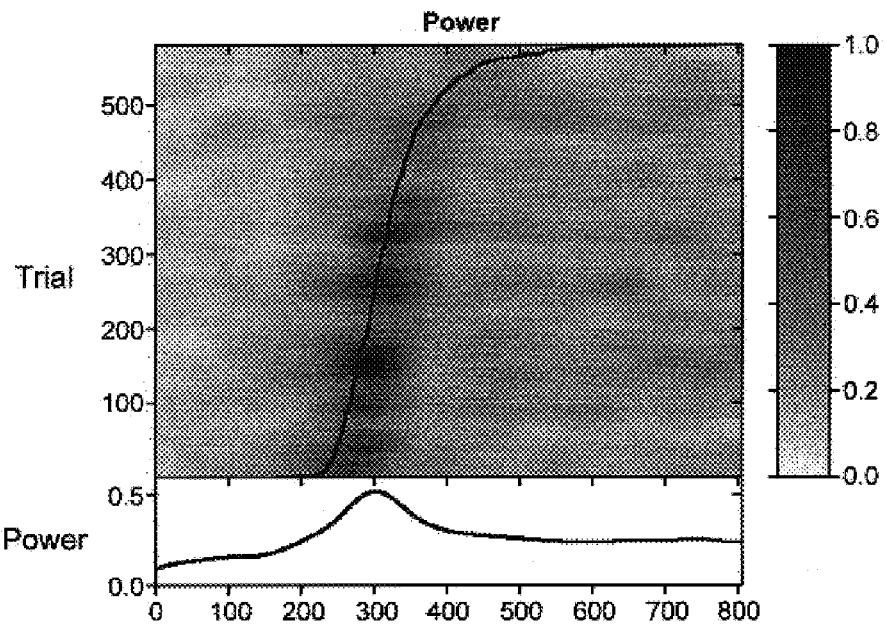
FIG. 16C is a representation of an ERP-image, according to one embodiment of the invention.
Figure 16D:
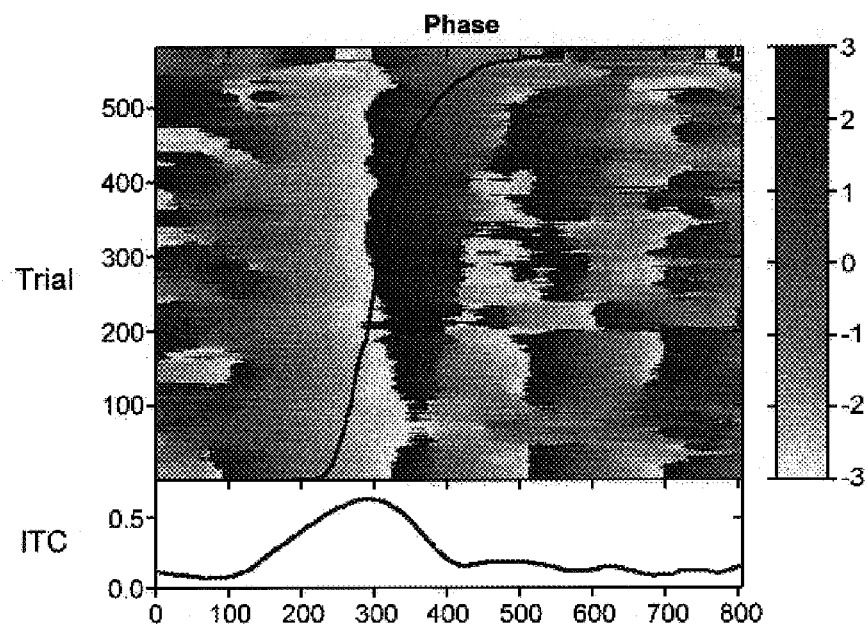
FIG. 16D is a representation of an ERP-image, according to one embodiment of the invention.

FIGS. 16A–D shows the independent component at 5 Hz obtained from fully-complex frequency-domain ICA, using the same dataset as for FIGS. 14 and 15. FIG. 16A shows the magnitude of the complex scalp map. FIG. 16B shows the imaginary part of the complex scalp map. FIG. 16C shows the ERP-images of 5-Hz power. FIG. 16D shows the complex-demodulated 5-Hz phase of the complex IC activation time-course. The magnitude map obtained by decomposing the 5-Hz band with the fully-complex ICA process, as shown in FIG. 16A, appears similar to the real-constrained component map. The corresponding imaginary map, as shown in FIG. 16B, has a non-negligible amplitude at the spatial focus of maximum scalp projection. This indicates that spatio-temporal dynamics may be present in the data, and that these dynamics may be modeled better with complex maps than with static real maps. Here, the complex IC magnitude, shown in FIG. 16C, and phase activations, shown in FIG. 16D, do not appear qualitatively different from the activations obtained with the real-map constrained-complex process, although the fully-complex ICA results in IC activations with a higher degree of independence than those obtained with real-map constrained-complex ICA.

Figure 17:
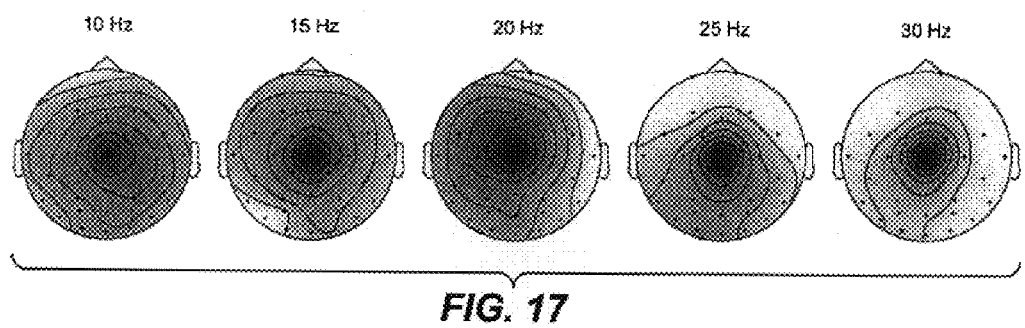
FIG. 17 is a representation of scalp maps, according to one embodiment of the invention.

To illustrate the similarity of component maps over different frequency bands, FIG. 17 displays those maps from the 10-Hz, 15 Hz, 20 Hz, 25 Hz, and 30-Hz decompositions that best match the illustrated 5-Hz component. FIG. 17 shows the magnitude maps of complex independent components obtained using the fully-complex frequency-domain ICA process at five frequency bands, using the same dataset as for FIGS. 14–16. The maps in FIG. 17 were obtained using the fully-complex ICA process, but only the magnitude maps are shown. While the site of maximum scalp projection remains similar, the maps exhibit differences in shape and spatial extent, further suggesting that the complex frequency-domain ICA process may model aspects of the data that standard ICA process ignore.

Applications to fMRI Data

As indicated above, the present invention can be applied functional magnetic resonance imaging (fMRI) data. Related embodiments are described below.

The blood oxygenation level dependent (BOLD) contrast measured by fMRI recordings is generally thought of as evoked by supply of oxygenated blood which, in turn, is triggered by neural activity. Oxygenated blood propagates from supply vessels to the active neural tissue. Therefore, it is plausible to hypothesize that patterns of spatio-temporally dynamic patterns may be found in fMRI recordings of brain activity.

The convolutive models discussed above provide a way to account for such flow patterns. Compared to EEG data, fMRI data are characterized by their high spatial resolution at a low temporal sampling rate. fMRI data are commonly analyzed by spatial ICA decomposition, where time-points correspond to input dimensions and voxels to samples. This is in contrast to temporal ICA used for EEG, where sensors constitute input dimensions and time-points samples. To apply complex ICA to fMRI signals, we analogously apply spatial complex ICA to frequency-domain fMRI data. With these modifications in mind, the above-described model characterizations are applicable to the analysis of fMRI data including models for frequency decompositions (Equations (1)–(2)), convolutive mixing models (Equations (3)–(5)), and complex ICA (Equations (6)–(14)).

The embodiments presented herein illustrate the applicability of the present invention to the analysis, characterization and monitoring of visual-stimulation fMRI data. The 250 s experimental session consisted of ten epochs with stimulus onset asynchrony (SOA) of 25 s. An 8 Hz flickering checkerboard stimulus was presented to one subject for 3.0 s at the beginning of each epoch. 500 time-points of data were recorded at a sampling rate of 2 Hz (TR=0.5) with resolution 64×64×5 voxels, field-of-view 250×250 mm, slice thickness 7 mm. Standard preprocessing included removal of off-brain and low-intensity voxels, reducing the data to 2863 voxels.

Spectral decomposition was performed using the windowed discrete Fourier transformation (1) with a Harming window of length 40 samples, a window shift of 1 sample, and frequency bands 0.05, 0.10, . . . , 1.00 Hz. This resulted in data split into 20 bands, each with 461 time-points and 2863 voxels.

Spatial complex ICA decomposition was performed within each frequency band. In a preprocessing step, input dimensionality in each band was reduced from 461 to 50 by retaining only the subspace spanned by the (complex) eigenvectors corresponding to the 50 largest eigenvalues of the data matrix X(f). Complex ICA decomposed this subspace into 50 complex independent components per band.

A relevant point of focus is the analysis of components with a region of activity (ROA) near primary visual cortex V1. One such component was found in several frequency bands, with a timecourse of activation that closely reflected the SOA of the visual stimulus. Time-locking of component activity to stimulus presentation was particularly reliable for component number 2 (IC2) in the 0.10 Hz band. The following analysis is restricted to this particular component.

Figure 18:
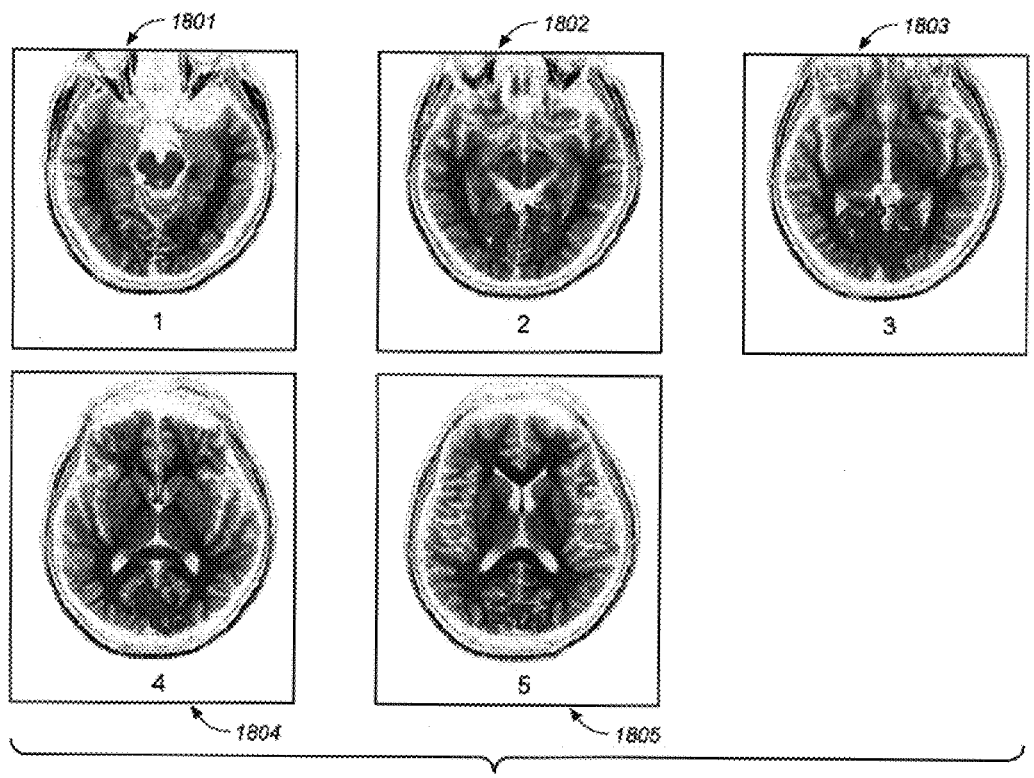
FIG. 18 is a representation of signal data, according to one embodiment of the invention directed to fMRI data.

FIG. 18 shows the magnitude of the complex spatial component map of IC2 in the ROA of the five recording slices 1801, 1802, 1803, 1804, 1805. The ROA was determined from z-scores of the component map by transforming each component map to zero mean and unit variance, and setting a heuristic threshold of 1.5. The extent of IC2 from the centrally located main blood vessels to primary visual cortex is clearly visible, in particular in the third slice 1903 and the fourth slice 1804. The complex component's phase in the ROA is displayed in FIG. 19 for the five recording slices 1901, 1902, 1903, 1904, 1905. The third slice 1903 and the fourth slice 1904 display a phase shift from the upper left border of the component ROA image towards the lower right border. The phase shift indicates a time lag in the activation of the component voxels when transformed back into the time-domain which will be further investigated below. A highlighted square 1906 in the fourth slice 1904 is a subject of more detailed analysis below.

Figure 20:
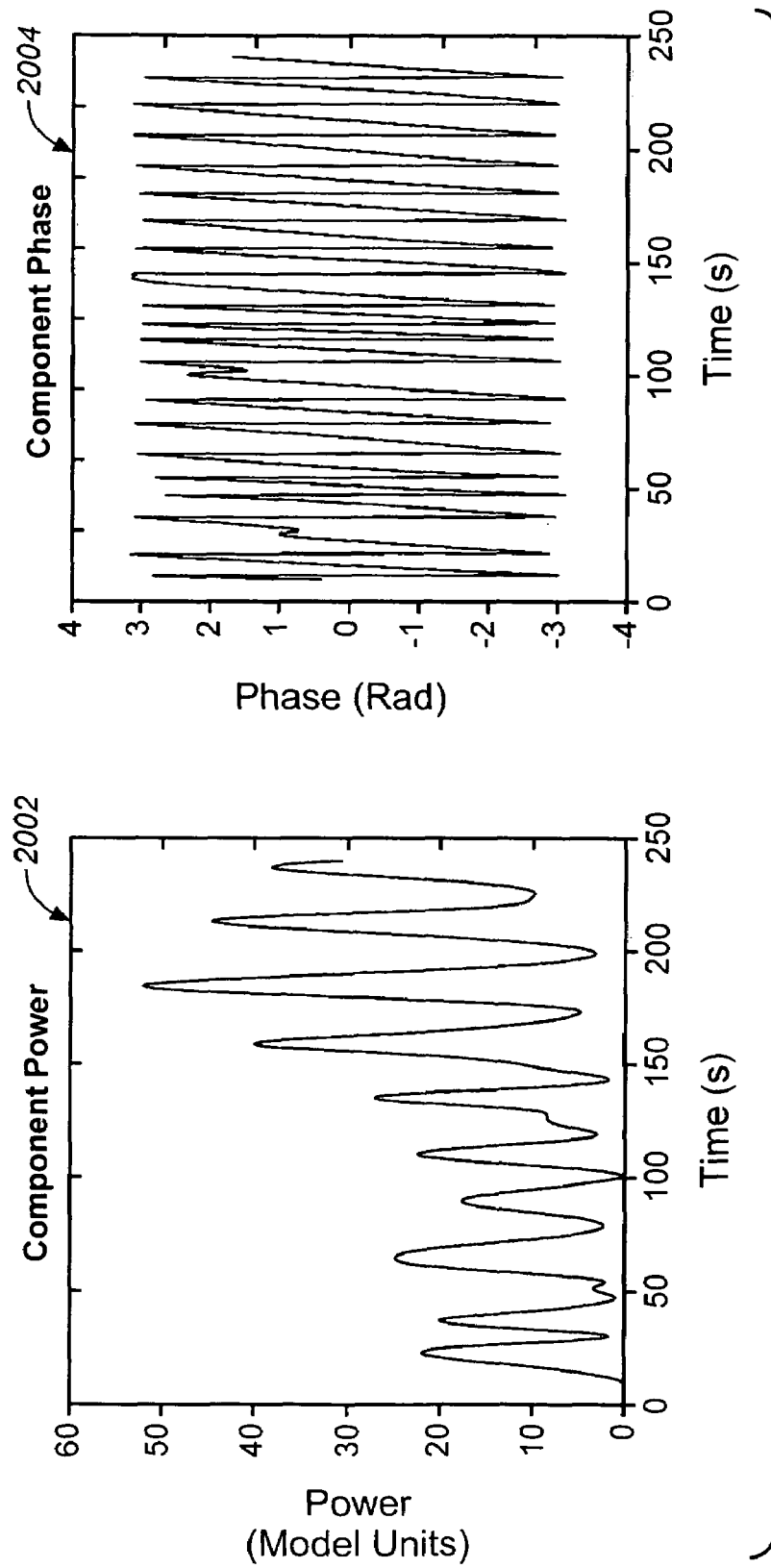
FIG. 20 is a representation of component power and phase, according to one embodiment of the invention directed to fMRI data.

FIG. 20 shows the time-course of power 2002 and phase 2004 of complex component IC2 in the 0.1 Hz frequency-band. Note the time-locking of amplitude and phase to stimulus presentation in 25 seconds intervals. The first and last 10 seconds of the experiment are not shown because computation of the spectral components was stopped when the analysis window (length 20 s) reached the edges of the recording. The time-interval from 179.5 s to 187.0 s is discussed further below with reference to FIG. 21. Component power 2002 clearly reflects the pattern of visual stimulation with an SOA of 25 s, with peaks in power that follow stimulation with a time lag of about 9 s, and a high dynamic range between component activity and inactivity. Component phase 2004 advances regularly and appears to be time locked to stimulus presentation, possibly to a lower degree during the periods from 0 s to 50 s and from 100 s to 130 s, which could be due to the subject's level of attention to the stimulus.

Complex voxel activity induced by the component may be obtained by backprojecting the complex time course to the complex spatial map, i.e., by forming the product $a_T(f)s_T(f)$, where T' denotes component number, $a_T(f)$ the corresponding column of the mixing matrix A(f), and $s_T(f)$ the corresponding row of the source matrix S(f). Transforming the complex frequency-domain voxel activity to the real time-domain voxel activity reduces-in the case of a window-shift of one sample and a single frequency band-to taking the real-part. We performed these steps to analyze time-domain voxel activity induced by the component in the time-range between 179.5 s and 187.0 s of the experiment.

Figure 19:
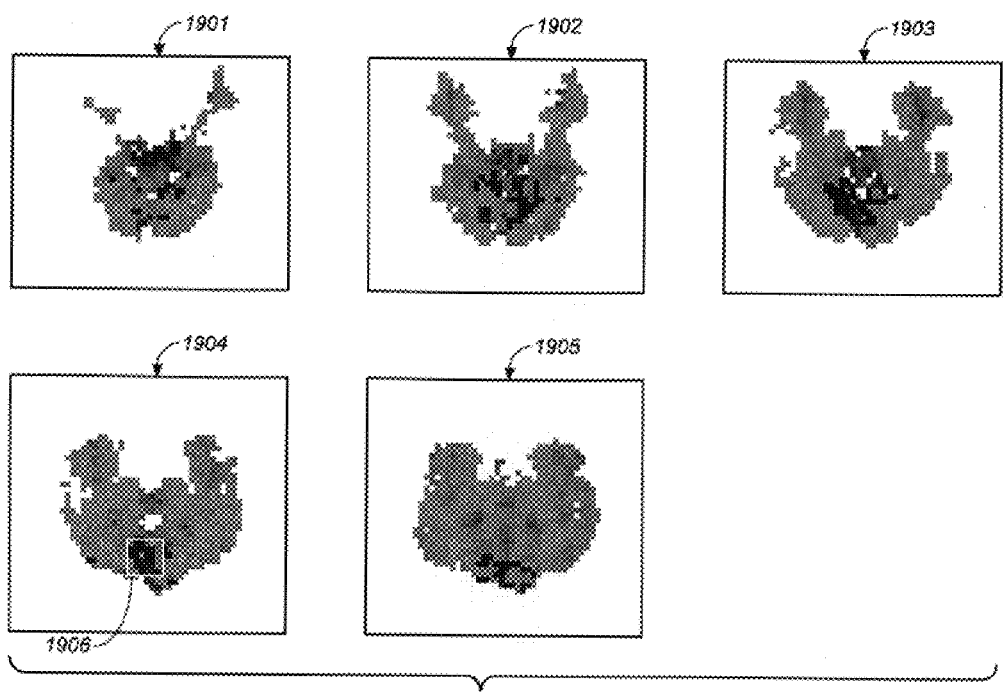
FIG. 19 is a representation of signal data, according to one embodiment of the invention directed to fMRI data.
Figure 21:
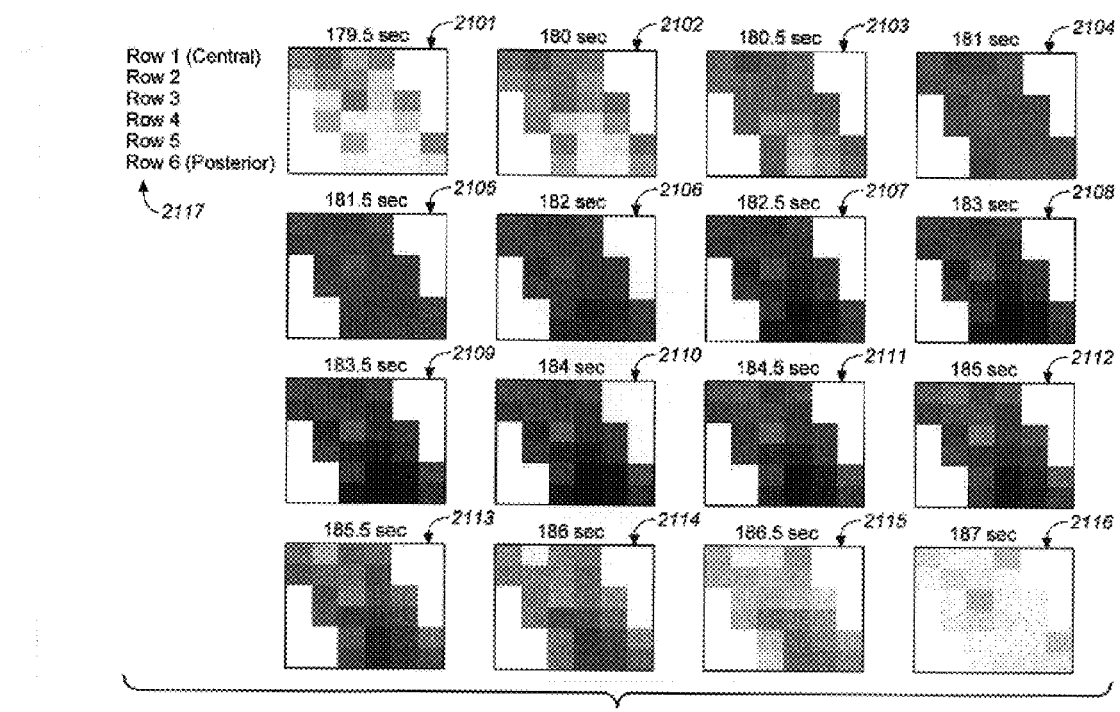
FIG. 21 is a representation of component activity, according to one embodiment of the invention directed to fMRI data

FIG. 21 displays the activity within a patch of 24 voxels located in the fourth recording slice 1904, marked by a black square 1906 in FIG. 19 (and corresponding to visual are V1). Following stimulus presentation at 175.0 s, activity in the patch is shown with representations of backprojected component activity from 179.5 s to 187 s in half-second increments 2101, 2102, 2103, 2104, 2105, 2106, 2107, 2108, 2109, 2110, 2111, 2112, 2113, 2114, 2115, 2116. Six rows 2117 are shown in the activity representation from row 1 (centrally located voxels) to row 6 (posterior voxels). To calculate these representations, a complex component time-course was backprojected to corresponding activity at the voxels and transformed to the time-domain. The flickering-checkerboard stimulus was presented for 3.0 s seconds at experiment time 175.0 s (not shown). Activation started to increase with a time-lag of about 4.5 s, with first increase occurring at the centrally-located voxels (top rows), and propagated to the posterior voxels (bottom rows) within approximately 1 s. This is compatible with over-supplied oxygenated blood propagating in the posterior direction and being washed out through the drainage vein from area V1.

As shown in FIG. 21, after stimulus presentation at 175.0 s, activity in the patch started to increase with a time lag of about 4.5 s, first in the voxels most centrally located in the brain (top row of voxels in each plot of FIG. 21), and propagating within about 1 s to the posterior voxels closest to primary visual cortex (bottom row of voxels in each plot of FIG. 21). Analogously, voxel activity decreased first in the top row of voxels before also decreasing in the bottom rows.

To compare time-lag effects in voxel activity induced by component IC2 in the 0.10-Hz frequency band versus voxel activity in the recorded data, we also computed the 0.10-Hz band activity of the recorded data at the 24 voxels that have been investigated in FIG. 21, using the same spectral decomposition that has been used for the complex ICA decomposition. Activity accounted for by IC2 and recorded data was separately averaged within each voxel row, starting with row 1 for the most centrally located voxels, and up to row 6 for the voxels in the posterior position. The resulting averages are plotted in FIG. 22 for component induced activity 2202 and recorded data 2204.

Figure 22:
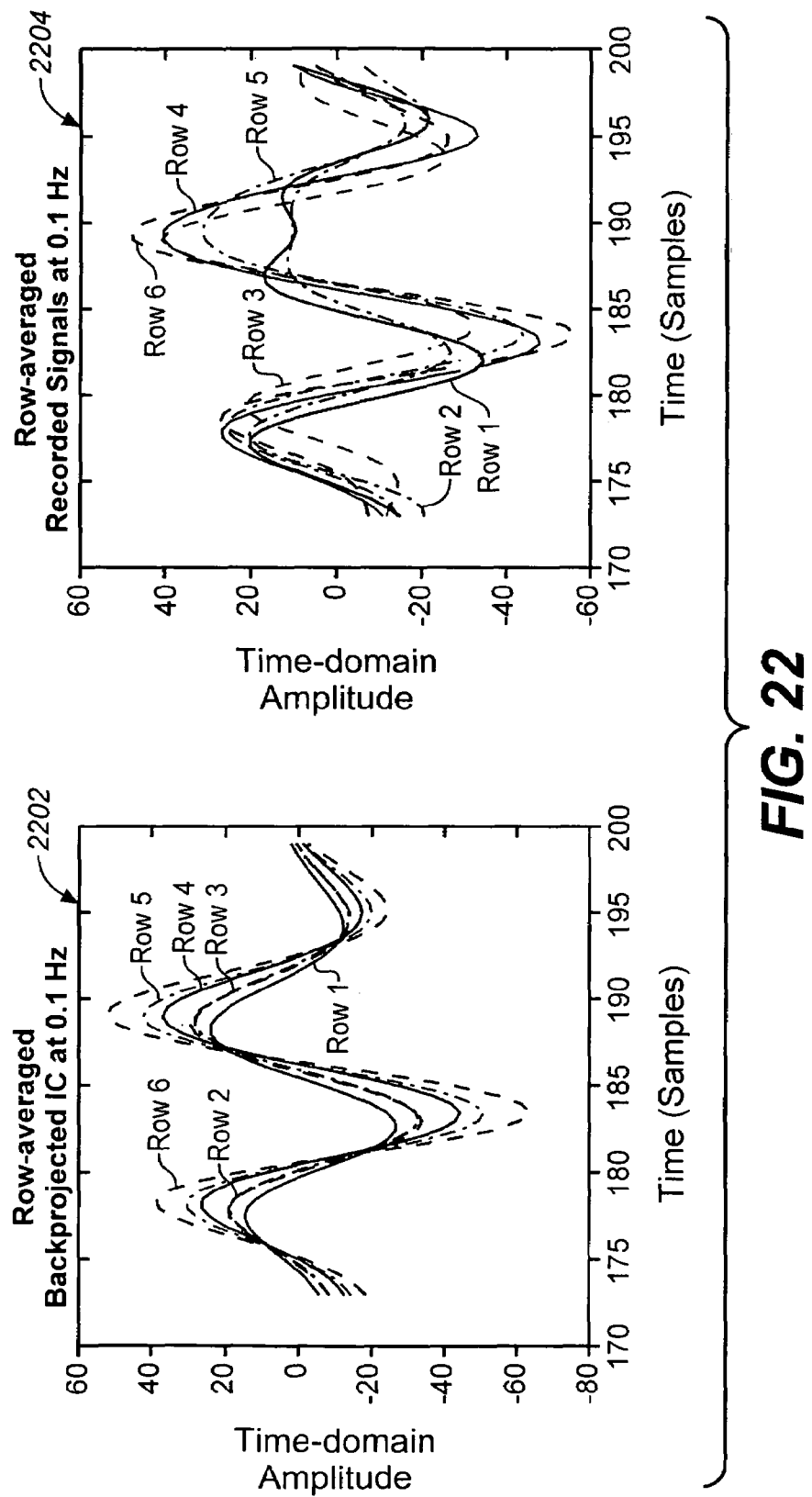
FIG. 22 is a representation of component and signal values, according to one embodiment of the invention directed to fMRI data

FIG. 22 shows a plot 2202 of time-courses for each row of 0.1 Hz band time-domain backprojected component activations displayed in FIG. 21. Each trace was computed by averaging over the timecourse of the four voxels in one row of FIG. 21. Row 1 corresponds to the most centrally located voxels, row 6 to the posterior row. FIG. 22 also shows a corresponding plot 2204 of average time-courses computed from the recorded activations in the 0.1 Hz band of the same voxels. For the average IC activation (left), the voxel-rows are activated in the order 1-(2,3)-(4, 5, 6) with row 6 being activated with a time-lag of about 1 second with respect to row 1. This lag is compatible with blood supply propagating across the patch in the posterior direction. In the average recorded activations (right), the voxel-rows are activated in the order 1-2-4-(5,6)-3. With the exception of row 3, this also indicates a posterior direction of propagation. The maximum time-lag in this case is 2 seconds. The most posterior voxel-row of backprojected component IC2 shows strongest activation which is plausible since it is closest to the drainage vein. The same tendency is found in the recorded signals, but ordering of amplitude of voxel-rows is not as monotonous as for IC2. Backprojected IC activations may represent a cleaner picture of the stimulus related process (both with respect to phase- and amplitude-gradient), because activity of other ongoing brain processes is canceled out.

Since the signals in FIG. 22 are band-limited, the oscillatory activity includes positive and negative swings. The analysis of relative time-lags and amplitudes near the peak of component power (at 184.5 s) is not influenced by this fact. In the component induced activity 2202, the more centrally located voxels are activated between 0.5 s and 1.0 s prior to the posterior voxels. The time-lag increases monotonously with more posterior voxel position. This gradient of posterior voxels being activated later than the central voxels is also reflected in the activity of the recorded voxels signals 2204. However, the voxels in row 3 form an exception since their extremal activation occurs even after the posterior voxels are activated. The analysis of activation amplitudes in FIG. 22 gives similar results: The component induced amplitude increases monotonously towards more posterior voxel position. Overall, this tendency is also found in the recorded signals, but some exceptions occur, e.g., amplitude in row 2 is smaller than in row 1.

As illustrated by the above embodiments, fMRI signals can be analyzed using a convolutive ICA approach that enables the modeling of patterns of spatio-temporal dynamics. Parameters for this model were efficiently estimated in the frequency-domain where the convolution factorizes into a product. For these embodiments, the underlying method includes three processing stages: 1) Computing time-frequency representations of the recorded signals, using short-term Fourier transformation. 2) Separation of the measured signals into independent components using spatial complex infomax ICA in each frequency band. 3) Computing the corresponding dynamic voxel activation pattern induced by each independent component in the time-domain.

From data of a visual stimulation fMRI experiment we obtained a complex component in the 0.1 Hz band with a component map ROA extending across primary visual cortex and its blood supply vessels. By reconstructing the spatio-temporal activation pattern accounted for by this component, we identified a time-lag of about 1 s between activation of central and posterior voxels. A related time-lag, but distributed less regularly, could be observed in the 0.1 Hz frequency-band of the measured signals. The amplitude of component-induced voxels activations increased in the posterior direction. Also this trend could be seen in the recorded signals, but it was less systematic than for the ICA processed signals.

Both observations are compatible with the physiology underlying generation of the fMRI signal. The posterior voxels in the component ROA are the ones closest to the posterior drainage vein. The convergence of over-supplied oxygenated blood towards the drainage vein may therefore result in the large amplitudes for these voxels. The temporal delay between activation of central and posterior voxels is consistent with the propagation of over-supplied oxygenated blood from the centrally located arteries to the posterior drainage vein.

These embodiments illustrate the ability of frequency-domain complex infomax ICA to capture patterns of spatio-temporal dynamics in fMRI data. It is reassuring that similar dynamics could also be observed in the recorded (mixed)

signals, making the possibility of the complex ICA results being mere processing artifacts implausible. On the other hand, the spatio-temporal dynamics emerged with a higher degree of regularity and physiological plausibility from the complex ICA results than from the measured data. Separation of the stimulus evoked activity from interfering, ongoing brain activity by the complex ICA method appears as the natural explanation for this observation.

Here, we have focused the analysis on a single frequency-band. Other embodiments focused on other frequency bands (e.g., frequency bands in which components have been found near V1) similarly enable reconstruction of the full time-domain spatio-temporal dynamics associated with visual stimulation.

CONCLUSION

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of monitoring signals, comprising:
   receiving signals from a plurality of sensors over a period of time;
   decomposing the signals into separate signal components within one or more frequency bands;
   selecting a frequency band within the one or more frequency bands;
   determining spatial and temporal characteristics of the signal components within the selected frequency band;
   isolating a subset of the signal components within the selected frequency band, based on the spatial and temporal characteristics of the signal components, to determine isolated signal components; and
   determining a location of a signal source corresponding to the isolated signal components.

2. The method of claim 1, wherein the signals include biological signals and the signal components include biological signal components.

3. The method of claim 2, wherein determining spatial and temporal characteristics of the biological signal components includes identifying a first biological signal component of the biological signal components, calculating a strength of the first biological signal component at a first time, and thereafter measuring to strength of said first biological signal component at a later time.

4. The method of claim 2, wherein decomposing the biological signals includes determining a phase and a magnitude characteristic for the biological signal components.

5. The method of claim 2, wherein the biological signals include at least one of electroencephalographic (EEG) signals, electrocardiographic (ECG) signals and electromyographic (EMG) signals.

6. The method of claim 2, wherein the biological signals include EEG signals, and the frequency band is selected from the group consisting of: delta, theta, alpha, sigma, beta, and gamma bands.

7. The method of claim 2, wherein the biological signals include functional magnetic resonance imaging (fMRI) signals.

8. The method of claim 1, wherein
   the selected frequency band is a first selected frequency band,
   the one or more frequency bands further include a second selected frequency band, and the method further comprises:
   determining spatial and temporal characteristics of the signal components within the second selected frequency band;
   isolating a subset of the signal components within the second selected frequency band, based on the spatial and temporal characteristics of the signal components, to determine isolated signal components; and
   matching at least some of the isolated signal components in the first selected frequency band with at least some of the isolated signal components in the second selected frequency band.

9. The method of claim 1, wherein determining spatial and temporal characteristics of the signal components includes identifying a convolutive mixing model for the signal components.

10. The method of claim 1, wherein at least one of the complex sources includes a complex-valued random variable having a circularly symmetric probability distribution.

11. The method of claim 1, wherein the spatial and temporal characteristics of the signal components within the selected frequency band include a separating matrix that relates the signal components within the selected frequency band to the complex sources.

12. The method of claim 11, wherein determining the spatial and temporal characteristics of the signal components within the selected frequency band includes determining the separating matrix by optimizing a likelihood function that relates the separating matrix, the complex sources, and the signal components within the selected frequency band.

13. The method of claim 11, wherein determining the spatial and temporal characteristics of the signal components within the selected frequency band includes constraining the mixing matrix to be real-valued.

14. The method of claim 1, wherein the spatial and temporal characteristics of the signal components within the selected frequency band include a mixing matrix that relates the complex sources to the signal components within the selected frequency band.

15. A system for monitoring biological signals, comprising:
   a plurality of sensors for receiving biological signals;
   a first memory configured to decompose the received plurality of signals into separate signal components within one or more frequency bands and select a first frequency band;
   a second memory configured to determine spatial and temporal characteristics of the biological signal components in the first frequency band;
   a third memory configured to isolate a subset of the biological signal components within the first frequency band, based on the spatial and temporal characteristics of the biological signal components, to obtain isolated biological signal components; and
   a fourth memory configured to determine a location of a signal source corresponding to the isolated biological signal components.

16. The system of claim 15, further comprising a display for displaying the isolated biological signal components.

17. The system of claim 15, further comprising a storage for storing the biological signals.

18. The system of claim 15, wherein the third memory is configured to isolate a subset of the biological signal components by maximizing the difference between subsets of biological signal components within the first frequency band.

19. The system of claim 15, wherein the second memory is configured to determine the spatial and temporal characteristics of the biological signal components by:
identifying a first biological signal component in the biological signal components,
calculating the strength of the first biological signal component at a first time, and
thereafter measuring the strength of said first biological signal component at a later time.

20. The system of claim 15, wherein the second memory is configured to determine the spatial and temporal characteristics of the biological signal components by identifying a convolutive mixing model for the biological signal components.

21. The system of claim 15, wherein the first memory is configured to decompose the biological signals by determining a phase characteristic and a magnitude characteristic for the biological signal components.

22. The system of claim 15, wherein at least two of the first memory, the second memory and the third memory are included in a common memory.

23. The system of claim 15, wherein at least one of the complex sources includes a complex-valued random variable having a circularly symmetric probability distribution.

24. The system of claim 15, wherein the spatial and temporal characteristics of the signal components within the selected frequency band include a separating matrix that relates the signal components within the selected frequency band to the complex sources.

25. The system of claim 24, wherein determining the spatial and temporal characteristics of the signal components within the selected frequency band includes determining the separating matrix by optimizing a likelihood function that relates the separating matrix, the complex sources, and the signal components within the selected frequency band.

26. The system of claim 24, wherein determining the spatial and temporal characteristics of the signal components within the selected frequency band includes constraining the mixing matrix to be real-valued.

27. The system of claim 15, wherein the spatial and temporal characteristics of the signal components within the selected frequency band include a mixing matrix that relates the complex sources to the signal components within the selected frequency band.

28. The system of claim 15, wherein
the first memory is further configured to select a second frequency band;
the second memory is further configured to determine spatial and temporal characteristics of the biological signal components in the second frequency band; and
the third memory is further configured
to isolate a subset of the biological signal components within the second frequency band, based on the spatial and temporal characteristics of the biological signal components, to obtain isolated biological signal components, and
to match at least some of the isolated signal components in the first selected frequency band with at least some of the isolated signal components in second selected frequency band.

29. A computer-readable medium that stores a computer program for monitoring signals, wherein the computer program includes instructions for:
receiving signals from a plurality of sensors over a period of time;
decomposing the signals into separate signal components within one or more frequency bands;
selecting a frequency band within the one or more frequency bands;
determining spatial and temporal characteristics of the signal components within the selected frequency band; and
isolating a subset of the signal components within the selected frequency band, based on the spatial and temporal characteristics of the signal components, to determine isolated signal components; and
determining a location of a signal source corresponding to the isolated signal components.

30. A method of monitoring signals, comprising:
receiving signals from a plurality of sensors over a period of time;
decomposing the signals into separate signal components within one or more frequency bands;
selecting a first frequency band within the one or more frequency bands;
determining spatial and temporal characteristics of the signal components within the first frequency band;
isolating a subset of the signal components within the first frequency band, based on the spatial and temporal characteristics of the signal components, to determine isolated signal components;
selecting a second frequency band within the one or more frequency bands;
determining spatial and temporal characteristics of the signal components within the second frequency band;
isolating a subset of the signal components within the second frequency band, based on the spatial and temporal characteristics of the signal components, to determine isolated signal components; and
matching at least some of the isolated signal components in the first frequency band with at least some of the isolated signal components in the second frequency band.

31. A system for monitoring signals, comprising:
a plurality of sensors for receiving signals;
a first memory configured to decompose the received plurality of signal into separate signal components within one or more frequency bands, select a first frequency band, and select a second frequency band;
a second memory configured to determine spatial and temporal characteristics of the signal components in the first frequency band and the second frequency band; and
a third memory configured;
to isolate a subset of the signal components within the first frequency band, based on the spatial and temporal characteristics of the biological signal components, to obtain isolated signal components,
to isolate a subset of the signal components within the second frequency band, based on the spatial and temporal characteristics of the biological signal components, to obtain isolated signal components, and
to match at least some of the isolated signal components in the first frequency band with at least some of the isolated signal components in second frequency band.

32. The method of claim 2, wherein the isolated subset of the signal components includes biological signal components and isolating the subset of the biological signal components includes maximizing differences between the subset of the biological signal components and other biological signal components within the selected frequency band.

* * * * *